(12) United States Patent
Pimenta (10) Patent No.: US 9,198,765 B1
(45) Date of Patent: Dec. 1, 2015

(54) EXPANDABLE SPINAL FUSION IMPLANTS AND RELATED METHODS (71) Applicant: NuVasive, Inc., San Diego, CA (US)

(72) Inventor: Luiz Pimenta, Sao Paulo (BR)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 13/665,787

(22) Filed: Oct. 31, 2012

Related U.S. Application Data (60) Provisional application No. 61/553,895, filed on Oct. 31, 2011.

(51) Int. Cl.
*A61F 2/44* (2006.01)

(52) U.S. Cl.
CPC ............. *A61F 2/44* (2013.01); *A61F 2/4455* (2013.01)

(58) Field of Classification Search
CPC ............ A61F 2002/30579; A61F 2002/30518; A61F 2002/3052; A61F 2002/30523; A61F 2002/3055; A61F 2002/30601; A61F 2002/30604; A61F 2002/30556; A61F 2250/0004; A61F 2250/0007; A61F 2250/0009; A61F 2/4455; A61F 2/447; A61F 2002/30975; A61F 2002/448
USPC ............................................. 623/17.11–17.16
See application file for complete search history.

(56) References Cited

U.S. PATENT DOCUMENTS

| | | | |
|---|---|---|---|
| 208,227 A | 9/1878 | Dorr | |
| 972,983 A | 10/1910 | Arthur | |
| 1,003,232 A | 10/1910 | Cerbo | |
| 1,044,348 A | 6/1912 | Cerbo | |
| 1,328,624 A | 1/1920 | Graham | |
| 1,548,184 A | 8/1925 | Cameron | |
| 1,919,120 A | 7/1933 | O'Connor et al. | |
| 2,594,086 A | 4/1952 | Smith | |
| 2,704,064 A | 3/1955 | Fizzell et al. | |
| 2,736,002 A | 2/1956 | Oriel | |
| 2,808,826 A | 10/1957 | Reiner et al. | |
| 3,364,929 A | 1/1968 | Ide et al. | |
| 3,486,505 A | 12/1969 | Morrison | |
| 3,518,993 A | 7/1970 | Blake | |
| 3,604,487 A | 9/1971 | Gilbert | |
| 3,664,329 A | 5/1972 | Naylor | |
| 3,682,162 A | 8/1972 | Colyer | |
| 3,745,995 A | 7/1973 | Kraus | |
| 3,785,368 A | 1/1974 | McCarthy et al. | |
| 3,803,716 A | 4/1974 | Garnier | |
| 3,830,226 A | 8/1974 | Staub et al. | |
| 3,848,601 A | 11/1974 | Ma et al. | |
| 3,867,728 A | 2/1975 | Stubstad et al. | |
| 3,957,036 A | 5/1976 | Normann | |

(Continued)

FOREIGN PATENT DOCUMENTS

CA 2015507 1/1999
CN 101972179 A 2/2011

(Continued)

OTHER PUBLICATIONS

Anatomy of the Lumbar Spine in MED TM MicroEndoscopic Discectomy (1997 Ludann Grand Rapids MI), 14 pgs.

(Continued)

*Primary Examiner* — Mary Hoffman
(74) *Attorney, Agent, or Firm* — Jonathan Spangler; Jennifer Russell (57) ABSTRACT

A system and methods for promoting fusion across an intervertebral disc space, the system including an expandable system of spinal fusion implants wherein the system of implants is inserted into an intervertebral disc space in a smaller profile, collapsed insertion state, and then expanded anteriorly to an expanded state.

8 Claims, 6 Drawing Sheets

(56) References Cited

U.S. PATENT DOCUMENTS

| | | |
|---|---|---|
| 4,026,304 A | 5/1977 | Levy |
| 4,026,305 A | 5/1977 | Brownlee et al. |
| D245,789 S | 9/1977 | Shea et al. |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,226,288 A | 10/1980 | Collins, Jr. |
| 4,235,242 A | 11/1980 | Howson et al. |
| 4,285,347 A | 8/1981 | Hess |
| 4,291,705 A | 9/1981 | Severinghaus et al. |
| 4,349,921 A | 9/1982 | Kuntz |
| 4,449,532 A | 5/1984 | Storz |
| 4,454,374 A | 6/1984 | Pollack |
| 4,461,300 A | 7/1984 | Christensen |
| 4,501,269 A | 2/1985 | Bagby |
| 4,512,351 A | 4/1985 | Pohndorf |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |
| 4,573,448 A | 3/1986 | Kambin |
| 4,592,369 A | 6/1986 | Davis et al. |
| 4,595,013 A | 6/1986 | Jones et al. |
| 4,595,018 A | 6/1986 | Rantala |
| 4,611,597 A | 9/1986 | Kraus |
| 4,616,635 A | 10/1986 | Caspar et al. |
| 4,633,889 A | 1/1987 | Talalla |
| 4,646,738 A | 3/1987 | Trott |
| 4,657,550 A | 4/1987 | Daher |
| 4,658,835 A | 4/1987 | Pohndorf |
| D295,445 S | 4/1988 | Freeman |
| 4,743,256 A | 5/1988 | Brantigan |
| 4,744,371 A | 5/1988 | Harris |
| 4,753,223 A | 6/1988 | Bremer |
| 4,759,377 A | 7/1988 | Dykstra |
| 4,781,591 A | 11/1988 | Allen |
| 4,784,150 A | 11/1988 | Voorhies et al. |
| 4,807,642 A | 2/1989 | Brown |
| D300,561 S | 4/1989 | Asa et al. |
| 4,834,757 A | 5/1989 | Brantigan |
| 4,863,476 A | 9/1989 | Shepperd |
| 4,877,020 A | 10/1989 | Vich |
| 4,878,915 A | 11/1989 | Brantigan |
| 4,892,105 A | 1/1990 | Prass |
| 4,913,134 A | 4/1990 | Luque |
| 4,917,274 A | 4/1990 | Asa et al. |
| 4,917,704 A | 4/1990 | Frey et al. |
| 4,926,865 A | 5/1990 | Oman |
| 4,932,975 A | 6/1990 | Main et al. |
| 4,950,257 A | 8/1990 | Hibbs et al. |
| 4,950,296 A | 8/1990 | McIntyre |
| 4,961,740 A | 10/1990 | Ray et al. |
| 4,962,766 A | 10/1990 | Herzon |
| 4,964,411 A | 10/1990 | Johnson et al. |
| 5,007,902 A | 4/1991 | Witt |
| 5,015,247 A | 5/1991 | Michelson |
| 5,026,373 A | 6/1991 | Ray et al. |
| 5,045,054 A | 9/1991 | Hood et al. |
| 5,047,055 A | 9/1991 | Bao et al. |
| 5,052,373 A | 10/1991 | Michelson |
| 5,055,104 A | 10/1991 | Ray |
| 5,058,602 A | 10/1991 | Brody |
| 5,059,193 A | 10/1991 | Kuslich |
| 5,062,845 A | 11/1991 | Kuslich et al. |
| 5,071,437 A | 12/1991 | Steffee |
| 5,081,990 A | 1/1992 | Deletis |
| 5,092,344 A | 3/1992 | Lee |
| 5,092,572 A | 3/1992 | Litwak et al. |
| 5,127,403 A | 7/1992 | Brownlee |
| 5,133,717 A | 7/1992 | Chopin |
| 5,133,755 A | 7/1992 | Brekke |
| 5,161,533 A | 11/1992 | Prass et al. |
| 5,171,278 A | 12/1992 | Pisharodi |
| 5,171,279 A | 12/1992 | Mathews |
| 5,192,327 A | 3/1993 | Brantigan |
| 5,195,541 A | 3/1993 | Obenchain |
| 5,196,015 A | 3/1993 | Neubardt |
| 5,215,100 A | 6/1993 | Spitz et al. |
| 5,217,497 A | 6/1993 | Mehdian |
| RE34,390 E | 9/1993 | Culver |
| D340,521 S | 10/1993 | Heinzelman et al. |
| 5,255,691 A | 10/1993 | Otten |
| 5,263,953 A | 11/1993 | Bagby |
| 5,269,785 A | 12/1993 | Bonutti |
| 5,282,468 A | 2/1994 | Klepinski |
| 5,284,153 A | 2/1994 | Raymond et al. |
| 5,284,154 A | 2/1994 | Raymond et al. |
| 5,290,494 A | 3/1994 | Coombes et al. |
| 5,295,994 A | 3/1994 | Bonutti |
| 5,299,563 A | 4/1994 | Seton |
| 5,300,076 A | 4/1994 | Leriche |
| 5,304,210 A | 4/1994 | Crook |
| 5,306,307 A | 4/1994 | Senter et al. |
| 5,306,309 A | 4/1994 | Wagner et al. |
| 5,312,417 A | 5/1994 | Wilk |
| 5,313,956 A | 5/1994 | Knutsson et al. |
| 5,313,962 A | 5/1994 | Obenchain |
| 5,322,505 A | 6/1994 | Krause et al. |
| 5,327,902 A | 7/1994 | Lemmen |
| 5,331,975 A | 7/1994 | Bonutti |
| 5,333,618 A | 8/1994 | Lekhtman et al. |
| 5,334,205 A | 8/1994 | Cain |
| 5,336,223 A | 8/1994 | Rogers |
| 5,342,384 A | 8/1994 | Sugarbaker |
| 5,357,983 A | 10/1994 | Mathews |
| 5,364,400 A | 11/1994 | Rego, Jr. et al. |
| 5,375,067 A | 12/1994 | Berchin |
| 5,375,594 A | 12/1994 | Cueva |
| 5,383,876 A | 1/1995 | Nardella |
| 5,390,683 A | 2/1995 | Pisharodi |
| 5,395,317 A | 3/1995 | Kambin |
| 5,395,372 A | 3/1995 | Holt et al. |
| 5,397,363 A | 3/1995 | Gelbard |
| 5,397,364 A | 3/1995 | Kozak |
| 5,405,391 A | 4/1995 | Hednerson et al. |
| 5,413,602 A | 5/1995 | Metz-Stavenhagen |
| 5,425,772 A | 6/1995 | Brantigan |
| 5,431,658 A | 7/1995 | Moskovich |
| 5,443,514 A | 8/1995 | Steffee |
| 5,443,515 A | 8/1995 | Cohen et al. |
| 5,445,639 A | 8/1995 | Kuslich et al. |
| 5,450,845 A | 9/1995 | Axelgaard |
| 5,454,811 A | 10/1995 | Huebner |
| 5,458,638 A | 10/1995 | Kuslich et al. |
| 5,472,426 A | 12/1995 | Bonati et al. |
| 5,474,057 A | 12/1995 | Makower et al. |
| 5,474,558 A | 12/1995 | Neubardt |
| 5,480,440 A | 1/1996 | Kambin |
| 5,482,038 A | 1/1996 | Ruff |
| 5,484,403 A | 1/1996 | Yoakum et al. |
| 5,484,437 A | 1/1996 | Michelson |
| 5,487,739 A | 1/1996 | Aebischer et al. |
| 5,489,307 A | 2/1996 | Kuslich et al. |
| 5,489,308 A | 2/1996 | Kuslich et al. |
| 5,509,893 A | 4/1996 | Pracas |
| 5,514,153 A | 5/1996 | Bonutti |
| 5,514,180 A | 5/1996 | Heggeness et al. |
| 5,522,879 A | 6/1996 | Scopelianos |
| 5,522,899 A | 6/1996 | Michelson |
| 5,524,624 A | 6/1996 | Tepper et al. |
| 5,527,312 A | 6/1996 | Ray |
| 5,534,030 A | 7/1996 | Navarro et al. |
| 5,540,235 A | 7/1996 | Wilson |
| 5,540,688 A | 7/1996 | Navas |
| 5,545,222 A | 8/1996 | Bonutti |
| 5,545,688 A | 8/1996 | Huang |
| 5,549,656 A | 8/1996 | Reiss |
| 5,560,372 A | 10/1996 | Cory |
| 5,562,736 A | 10/1996 | Ray et al. |
| 5,565,005 A | 10/1996 | Erickson et al. |
| 5,566,678 A | 10/1996 | Cadwell |

(56) References Cited

U.S. PATENT DOCUMENTS

| | | |
|---|---|---|
| 5,569,290 A | 10/1996 | McAfee |
| 5,571,149 A | 11/1996 | Liss et al. |
| 5,571,190 A | 11/1996 | Ulrich |
| 5,571,192 A | 11/1996 | Schonhoffer |
| 5,579,781 A | 12/1996 | Cooke |
| 5,593,409 A | 1/1997 | Michelson |
| 5,593,429 A | 1/1997 | Ruff |
| 5,596,325 A | 1/1997 | Maas |
| 5,599,279 A | 2/1997 | Slotman et al. |
| 5,607,424 A | 3/1997 | Tropiano |
| 5,609,636 A | 3/1997 | Kohrs et al. |
| 5,611,800 A | 3/1997 | Davis et al. |
| 5,611,810 A | 3/1997 | Arnold et al. |
| 5,630,813 A | 5/1997 | Kieturakis |
| 5,632,747 A | 5/1997 | Scarborough et al. |
| 5,645,596 A | 7/1997 | Kim et al. |
| 5,645,598 A | 7/1997 | Brosnahan et al. |
| 5,653,761 A | 8/1997 | Pisharodi |
| 5,653,762 A | 8/1997 | Pisharodi |
| 5,658,336 A | 8/1997 | Pisharodi |
| 5,658,337 A | 8/1997 | Kohrs et al. |
| 5,662,710 A | 9/1997 | Bonutti |
| 5,665,122 A | 9/1997 | Kambin |
| 5,667,508 A | 9/1997 | Errico et al. |
| 5,669,909 A | 9/1997 | Zdeblick et al. |
| 5,671,752 A | 9/1997 | Sinderby et al. |
| 5,676,703 A | 10/1997 | Gelbard |
| 5,681,265 A | 10/1997 | Maeda et al. |
| 5,683,394 A | 11/1997 | Rinner |
| 5,683,400 A | 11/1997 | McGuire |
| 5,683,464 A | 11/1997 | Wagner et al. |
| 5,688,223 A | 11/1997 | Rosendahl |
| 5,690,629 A | 11/1997 | Asher et al. |
| 5,693,100 A | 12/1997 | Pisharodi |
| 5,700,264 A | 12/1997 | Zucherman et al. |
| 5,700,291 A | 12/1997 | Kuslich et al. |
| 5,700,292 A | 12/1997 | Margulies |
| 5,702,449 A | 12/1997 | McKay |
| 5,702,451 A | 12/1997 | Biedermann et al. |
| 5,702,453 A | 12/1997 | Rabbe et al. |
| 5,702,454 A | 12/1997 | Baumgartner |
| 5,702,455 A | 12/1997 | Saggar |
| 5,703,451 A | 12/1997 | Yamamichi et al. |
| 5,707,359 A | 1/1998 | Bufalini |
| 5,707,373 A | 1/1998 | Sevrain et al. |
| 5,711,307 A | 1/1998 | Smits |
| 5,711,957 A | 1/1998 | Patat et al. |
| 5,716,415 A | 2/1998 | Steffee |
| 5,720,748 A | 2/1998 | Kuslich et al. |
| 5,720,751 A | 2/1998 | Jackson |
| 5,728,046 A | 3/1998 | Mayer et al. |
| 5,728,159 A | 3/1998 | Stroever et al. |
| 5,741,253 A | 4/1998 | Michelson |
| 5,741,261 A | 4/1998 | Moskovitz et al. |
| 5,755,797 A | 5/1998 | Baumgartner |
| 5,759,159 A | 6/1998 | Masreliez |
| 5,762,629 A | 6/1998 | Kambin |
| 5,766,252 A | 6/1998 | Henry et al. |
| 5,772,661 A | 6/1998 | Michelson |
| 5,775,331 A | 7/1998 | Raymond et al. |
| 5,775,797 A | 7/1998 | Henstra |
| 5,776,144 A | 7/1998 | Leysieffer et al. |
| 5,779,642 A | 7/1998 | Nightengale |
| 5,782,830 A | 7/1998 | Farris |
| 5,782,919 A | 7/1998 | Zdeblick et al. |
| 5,785,658 A | 7/1998 | Benaron |
| 5,785,710 A | 7/1998 | Michelson |
| 5,792,044 A | 8/1998 | Foley et al. |
| 5,797,854 A | 8/1998 | Hedgecock |
| 5,797,909 A | 8/1998 | Michelson |
| 5,800,549 A | 9/1998 | Bao et al. |
| 5,800,550 A | 9/1998 | Sertich |
| 5,814,073 A | 9/1998 | Bonutti |
| 5,814,084 A | 9/1998 | Grivas et al. |
| 5,814,550 A | 9/1998 | Wolcott |
| 5,830,151 A | 11/1998 | Hadzic et al. |
| 5,851,084 A | 12/1998 | Nishikawa |
| 5,851,191 A | 12/1998 | Gozani |
| 5,851,208 A | 12/1998 | Trott |
| 5,853,373 A | 12/1998 | Griffith et al. |
| 5,860,973 A | 1/1999 | Michelson |
| 5,861,041 A | 1/1999 | Tienboon |
| 5,862,314 A | 1/1999 | Jeddeloh |
| 5,865,845 A | 2/1999 | Thalgott |
| 5,865,848 A | 2/1999 | Baker |
| 5,872,314 A | 2/1999 | Clinton |
| 5,885,210 A | 3/1999 | Cox |
| 5,885,219 A | 3/1999 | Nightengale |
| 5,885,299 A | 3/1999 | Winslow et al. |
| 5,888,196 A | 3/1999 | Bonutti |
| 5,888,219 A | 3/1999 | Bonutti |
| 5,888,224 A | 3/1999 | Beckers et al. |
| 5,891,147 A | 4/1999 | Moskovitz et al. |
| 5,893,890 A | 4/1999 | Pisharodi |
| 5,902,231 A | 5/1999 | Foley et al. |
| 5,904,719 A | 5/1999 | Errico et al. |
| 5,910,315 A | 6/1999 | Stevenson et al. |
| 5,928,139 A | 7/1999 | Koros et al. |
| 5,928,158 A | 7/1999 | Aristides |
| 5,931,777 A | 8/1999 | Sava |
| 5,935,131 A | 8/1999 | Bonutti et al. |
| 5,938,688 A | 8/1999 | Schiff |
| 5,942,698 A | 8/1999 | Stevens |
| 5,944,658 A | 8/1999 | Koros et al. |
| 5,954,769 A | 9/1999 | Rosenlicht |
| 5,968,098 A | 10/1999 | Winslow |
| 5,976,094 A | 11/1999 | Gozani et al. |
| 5,993,474 A | 11/1999 | Ouchi |
| 6,003,426 A | 12/1999 | Kobayashi et al. |
| 6,004,262 A | 12/1999 | Putz et al. |
| 6,004,312 A | 12/1999 | Finneran |
| 6,004,326 A | 12/1999 | Castro et al. |
| 6,007,487 A | 12/1999 | Foley et al. |
| 6,008,433 A | 12/1999 | Stone |
| 6,010,520 A | 1/2000 | Pattison |
| 6,015,436 A | 1/2000 | Schunhuffer |
| 6,019,793 A | 2/2000 | Perren et al. |
| 6,024,696 A | 2/2000 | Hoftman et al. |
| 6,024,697 A | 2/2000 | Pisarik |
| 6,027,456 A | 2/2000 | Feler et al. |
| 6,033,405 A | 3/2000 | Winslow et al. |
| 6,033,438 A | 3/2000 | Bianchi et al. |
| 6,038,469 A | 3/2000 | Karlsson et al. |
| 6,038,477 A | 3/2000 | Kayyali |
| 6,039,761 A | 3/2000 | Li et al. |
| 6,042,582 A | 3/2000 | Ray |
| 6,045,580 A | 4/2000 | Scarborough et al. |
| 6,045,582 A | 4/2000 | Prybyla |
| 6,048,342 A | 4/2000 | Zucherman et al. |
| 6,050,992 A | 4/2000 | Nichols |
| 6,059,829 A | 5/2000 | Schlapfer et al. |
| 6,063,088 A | 5/2000 | Winslow |
| 6,074,343 A | 6/2000 | Nathanson et al. |
| 6,080,105 A | 6/2000 | Spears |
| 6,080,155 A | 6/2000 | Michelson |
| 6,083,154 A | 7/2000 | Liu et al. |
| 6,083,225 A | 7/2000 | Winslow et al. |
| 6,095,987 A | 8/2000 | Shmulewitz |
| 6,096,080 A | 8/2000 | Nicholson et al. |
| 6,102,948 A | 8/2000 | Brosnahan, III |
| 6,104,957 A | 8/2000 | Alo et al. |
| 6,104,960 A | 8/2000 | Duysens et al. |
| 6,110,210 A * | 8/2000 | Norton et al. ............... 623/17.16 |
| 6,113,639 A | 9/2000 | Ray et al. |
| 6,120,503 A | 9/2000 | Michelson |
| 6,120,506 A | 9/2000 | Kohrs et al. |
| 6,126,660 A | 10/2000 | Dietz |
| 6,126,689 A | 10/2000 | Brett |
| 6,132,386 A | 10/2000 | Gozani et al. |
| 6,132,387 A | 10/2000 | Gozani et al. |
| 6,132,472 A | 10/2000 | Bonutti |
| 6,135,965 A | 10/2000 | Tumer et al. |
| 6,139,493 A | 10/2000 | Koros et al. |
| 6,143,033 A | 11/2000 | Paul et al. |

(56) References Cited

U.S. PATENT DOCUMENTS

| | | | |
|---|---|---|---|
| 6,146,335 A | 11/2000 | Gozani | |
| 6,152,871 A | 11/2000 | Foley et al. | |
| 6,159,179 A | 12/2000 | Simonson | |
| 6,159,211 A | 12/2000 | Boriani et al. | |
| 6,159,215 A | 12/2000 | Urbahns et al. | |
| 6,161,047 A | 12/2000 | King et al. | |
| 6,174,311 B1 | 1/2001 | Branch et al. | |
| 6,181,961 B1 | 1/2001 | Prass | |
| 6,193,756 B1 | 2/2001 | Studer et al. | |
| 6,193,757 B1 * | 2/2001 | Foley et al. | 623/17.16 |
| 6,196,969 B1 | 3/2001 | Bester et al. | |
| 6,200,347 B1 | 3/2001 | Anderson et al. | |
| 6,206,826 B1 | 3/2001 | Mathews et al. | |
| 6,206,923 B1 * | 3/2001 | Boyd et al. | 623/17.11 |
| 6,217,509 B1 | 4/2001 | Foley et al. | |
| 6,224,549 B1 | 5/2001 | Drongelen | |
| 6,224,607 B1 | 5/2001 | Michelson | |
| 6,224,631 B1 | 5/2001 | Kohrs | |
| 6,241,769 B1 | 6/2001 | Nicholson et al. | |
| 6,241,770 B1 | 6/2001 | Michelson | |
| 6,241,771 B1 | 6/2001 | Gresser et al. | |
| 6,245,082 B1 | 6/2001 | Gellman et al. | |
| 6,251,140 B1 | 6/2001 | Marino et al. | |
| 6,258,125 B1 | 7/2001 | Paul et al. | |
| 6,259,945 B1 | 7/2001 | Epstein et al. | |
| 6,264,651 B1 | 7/2001 | Underwood et al. | |
| 6,264,655 B1 | 7/2001 | Pisharodi | |
| 6,266,558 B1 | 7/2001 | Gozani et al. | |
| 6,273,905 B1 | 8/2001 | Streeter | |
| 6,277,149 B1 | 8/2001 | Boyle et al. | |
| 6,292,701 B1 | 9/2001 | Prass et al. | |
| 6,304,487 B1 | 10/2001 | Pawletko et al. | |
| 6,306,100 B1 | 10/2001 | Prass | |
| 6,308,712 B1 | 10/2001 | Shaw | |
| 6,312,392 B1 | 11/2001 | Herzon | |
| 6,319,257 B1 | 11/2001 | Carignan et al. | |
| 6,325,764 B1 | 12/2001 | Griffith et al. | |
| 6,334,068 B1 | 12/2001 | Hacker | |
| 6,348,058 B1 | 2/2002 | Melkent et al. | |
| 6,360,750 B1 | 3/2002 | Gerber et al. | |
| 6,371,968 B1 | 4/2002 | Kogasaka et al. | |
| 6,371,989 B1 | 4/2002 | Chauvin et al. | |
| 6,383,221 B1 | 5/2002 | Scarborough et al. | |
| 6,387,130 B1 | 5/2002 | Stone et al. | |
| 6,395,007 B1 | 5/2002 | Bhatnagar et al. | |
| 6,409,766 B1 | 6/2002 | Brett | |
| 6,425,772 B1 | 7/2002 | Bernier et al. | |
| 6,425,859 B1 | 7/2002 | Foley et al. | |
| 6,425,887 B1 | 7/2002 | McGuckin et al. | |
| 6,425,901 B1 | 7/2002 | Zhu et al. | |
| 6,426,772 B1 | 7/2002 | Yoneyama et al. | |
| 6,432,140 B1 | 8/2002 | Lin | |
| 6,440,142 B1 | 8/2002 | Ralph et al. | |
| 6,442,814 B1 | 9/2002 | Landry et al. | |
| 6,447,547 B1 | 9/2002 | Michelson | |
| 6,450,952 B1 | 9/2002 | Rioux et al. | |
| 6,451,015 B1 | 9/2002 | Rittman, III et al. | |
| 6,454,806 B1 | 9/2002 | Cohen et al. | |
| 6,466,817 B1 | 10/2002 | Kaula et al. | |
| 6,468,205 B1 | 10/2002 | Mollenauer et al. | |
| 6,468,207 B1 | 10/2002 | Fowler, Jr. | |
| 6,468,311 B2 | 10/2002 | Boyd et al. | |
| 6,491,724 B1 | 12/2002 | Ferree | |
| 6,500,116 B1 | 12/2002 | Knapp | |
| 6,500,128 B2 | 12/2002 | Marino | |
| 6,520,907 B1 | 2/2003 | Foley et al. | |
| 6,524,320 B2 | 2/2003 | DiPoto | |
| 6,527,773 B1 | 3/2003 | Lin et al. | |
| 6,535,759 B1 | 3/2003 | Epstein et al. | |
| 6,537,320 B1 | 3/2003 | Michelson | |
| D472,634 S | 4/2003 | Anderson | |
| D473,650 S | 4/2003 | Anderson | |
| 6,547,823 B2 | 4/2003 | Scarborough et al. | |
| 6,558,424 B2 | 5/2003 | Thalgott | |
| 6,562,072 B1 | 5/2003 | Fuss et al. | |
| 6,564,078 B1 | 5/2003 | Marino et al. | |
| 6,579,244 B2 | 6/2003 | Goodwin | |
| 6,595,998 B2 | 7/2003 | Johnson et al. | |
| 6,599,294 B2 | 7/2003 | Fuss et al. | |
| 6,613,089 B1 | 9/2003 | Estes et al. | |
| 6,620,157 B1 | 9/2003 | Dabney et al. | |
| 6,620,196 B1 | 9/2003 | Trieu | |
| 6,626,905 B1 | 9/2003 | Schmiel et al. | |
| 6,635,086 B2 | 10/2003 | Lin | |
| 6,645,194 B2 | 11/2003 | Briscoe et al. | |
| 6,648,895 B2 | 11/2003 | Burkus et al. | |
| 6,672,019 B1 | 1/2004 | Wenz | |
| 6,676,665 B2 | 1/2004 | Foley et al. | |
| 6,676,703 B2 | 1/2004 | Biscup | |
| 6,679,833 B2 | 1/2004 | Smith et al. | |
| 6,706,067 B2 | 3/2004 | Shimp et al. | |
| 6,719,692 B2 | 4/2004 | Kleffner et al. | |
| 6,723,097 B2 | 4/2004 | Fraser et al. | |
| 6,723,126 B1 | 4/2004 | Berry | |
| 6,743,255 B2 | 6/2004 | Ferree | |
| 6,746,484 B1 | 6/2004 | Liu et al. | |
| 6,755,841 B2 | 6/2004 | Fraser et al. | |
| 6,760,616 B2 | 7/2004 | Hoey et al. | |
| 6,761,739 B2 | 7/2004 | Shepard | |
| 6,770,074 B2 | 8/2004 | Michelson | |
| 6,796,985 B2 | 9/2004 | Bolger et al. | |
| 6,810,281 B2 | 10/2004 | Brock et al. | |
| 6,819,956 B2 | 11/2004 | DiLorenzo | |
| 6,824,564 B2 | 11/2004 | Crozet | |
| 6,829,508 B2 | 12/2004 | Schulman et al. | |
| 6,830,570 B1 | 12/2004 | Frey et al. | |
| 6,833,006 B2 | 12/2004 | Foley et al. | |
| 6,847,849 B2 | 1/2005 | Mamo et al. | |
| 6,849,047 B2 | 2/2005 | Goodwin | |
| 6,855,105 B2 | 2/2005 | Jackson, III et al. | |
| 6,855,167 B2 | 2/2005 | Shimp et al. | |
| 6,855,168 B2 | 2/2005 | Crozet | |
| 6,869,398 B2 | 3/2005 | Obenchain | |
| 6,871,099 B1 | 3/2005 | Whitehurst et al. | |
| D503,801 S | 4/2005 | Jackson | |
| 6,902,569 B2 | 6/2005 | Parmer et al. | |
| 6,902,578 B1 | 6/2005 | Anderson et al. | |
| 6,913,621 B2 | 7/2005 | Boyd et al. | |
| 6,916,330 B2 | 7/2005 | Simonson | |
| 6,923,814 B1 | 8/2005 | Hildebrand et al. | |
| 6,926,728 B2 | 8/2005 | Zucherman et al. | |
| 6,929,606 B2 | 8/2005 | Ritland | |
| 6,936,070 B1 | 8/2005 | Muhanna | |
| 6,942,697 B2 | 9/2005 | Lange et al. | |
| 6,942,698 B1 | 9/2005 | Jackson | |
| 6,945,933 B2 | 9/2005 | Branch | |
| 6,951,538 B2 | 10/2005 | Ritland | |
| 6,964,687 B1 | 11/2005 | Bernard et al. | |
| 6,974,480 B2 | 12/2005 | Messerli et al. | |
| 6,979,353 B2 | 12/2005 | Bresina | |
| 6,984,245 B2 | 1/2006 | McGahan et al. | |
| 6,986,788 B2 | 1/2006 | Paul et al. | |
| 6,989,031 B2 | 1/2006 | Michelson | |
| 7,018,413 B2 | 3/2006 | Kruger | |
| 7,018,416 B2 | 3/2006 | Hanson et al. | |
| 7,037,339 B2 | 5/2006 | Houfburg | |
| 7,047,082 B1 | 5/2006 | Schrom et al. | |
| 7,050,848 B2 | 5/2006 | Hoey et al. | |
| 7,079,883 B2 | 7/2006 | Marino et al. | |
| 7,083,650 B2 | 8/2006 | Moskowitz et al. | |
| 7,087,055 B2 | 8/2006 | Lim et al. | |
| 7,089,059 B1 | 8/2006 | Pless | |
| D530,423 S | 10/2006 | Miles et al. | |
| 7,125,425 B2 | 10/2006 | Foley et al. | |
| 7,177,677 B2 | 2/2007 | Kaula et al. | |
| 7,192,447 B2 | 3/2007 | Rhoda | |
| 7,196,907 B2 | 3/2007 | Zheng | |
| 7,198,598 B2 | 4/2007 | Smith et al. | |
| 7,207,949 B2 | 4/2007 | Miles et al. | |
| 7,214,243 B2 | 5/2007 | Taylor | |
| 7,226,451 B2 | 6/2007 | Shluzas et al. | |
| 7,232,463 B2 | 6/2007 | Falahee | |
| 7,244,258 B2 | 7/2007 | Burkus et al. | |
| 7,255,532 B2 | 8/2007 | Zheng | |

(56) References Cited

U.S. PATENT DOCUMENTS

| | | |
|---|---|---|
| 7,261,688 B2 | 8/2007 | Smith et al. |
| 7,267,690 B2 | 9/2007 | Felt et al. |
| 7,303,583 B1 | 12/2007 | Schaer et al. |
| 7,318,839 B2 | 1/2008 | Malberg et al. |
| 7,326,251 B2 | 2/2008 | McCombe et al. |
| 7,396,365 B2 | 7/2008 | Michelson |
| 7,407,513 B2 | 8/2008 | Alleyne et al. |
| 7,442,210 B2 | 10/2008 | Segal et al. |
| 7,470,236 B1 | 12/2008 | Kelleher et al. |
| 7,473,222 B2 | 1/2009 | Dewey et al. |
| 7,481,766 B2 | 1/2009 | Lee et al. |
| 7,481,840 B2 | 1/2009 | Zucherman et al. |
| 7,497,868 B2 | 3/2009 | Steinberg |
| 7,503,920 B2 | 3/2009 | Siegal |
| 7,522,953 B2 | 4/2009 | Kaula et al. |
| 7,556,601 B2 | 7/2009 | Branch et al. |
| 7,582,058 B1 | 9/2009 | Miles et al. |
| 7,621,956 B2 | 11/2009 | Paul et al. |
| 7,621,960 B2 | 11/2009 | Boyd et al. |
| 7,625,377 B2 | 12/2009 | Veldhuizen et al. |
| 7,632,312 B2 | 12/2009 | Leclercq |
| 7,643,884 B2 | 1/2010 | Pond et al. |
| 7,655,042 B2 | 2/2010 | Foley et al. |
| 7,682,394 B2 | 3/2010 | Recoules-Arche et al. |
| 7,690,381 B2 | 4/2010 | Bartish et al. |
| 7,691,057 B2 | 4/2010 | Miles et al. |
| 7,693,562 B2 | 4/2010 | Marino et al. |
| 7,717,959 B2 | 5/2010 | William et al. |
| 7,727,279 B2 | 6/2010 | Zipnick et al. |
| 7,731,751 B2 | 6/2010 | Butler et al. |
| 7,758,644 B2 | 7/2010 | Trieu |
| 7,763,028 B2 | 7/2010 | Lim et al. |
| 7,819,801 B2 | 10/2010 | Miles et al. |
| 7,823,938 B2 | 11/2010 | McKee et al. |
| 7,846,206 B2 | 12/2010 | Oglaza et al. |
| 7,850,734 B2 | 12/2010 | Oh et al. |
| 7,854,766 B2 | 12/2010 | Moskowitz et al. |
| 7,857,818 B2 | 12/2010 | Trieu et al. |
| 7,867,277 B1 | 1/2011 | Tohmeh |
| 7,879,103 B2 | 2/2011 | Gertzman et al. |
| 7,887,589 B2 | 2/2011 | Glenn et al. |
| 7,887,593 B2 | 2/2011 | McKay et al. |
| 7,905,920 B2 | 3/2011 | Galea |
| 7,918,874 B2 | 4/2011 | Siegal |
| 7,935,051 B2 | 5/2011 | Miles et al. |
| 7,947,078 B2 | 5/2011 | Siegal |
| 7,951,199 B2 * | 5/2011 | Miller .................... 623/17.11 |
| 7,951,203 B2 | 5/2011 | Mccombe et al. |
| 7,959,652 B2 | 6/2011 | Zucherman et al. |
| 7,959,676 B2 | 6/2011 | Thramann |
| 7,988,735 B2 | 8/2011 | Yurek et al. |
| 7,993,403 B2 | 8/2011 | Foley et al. |
| 8,000,782 B2 | 8/2011 | Gharib et al. |
| 8,002,831 B2 | 8/2011 | Burd et al. |
| 8,002,833 B2 | 8/2011 | Fabris et al. |
| 8,005,535 B2 | 8/2011 | Gharib et al. |
| 8,007,532 B2 | 8/2011 | Manders |
| 8,007,535 B2 | 8/2011 | Hudgins et al. |
| 8,021,429 B2 | 9/2011 | Viker |
| 8,021,430 B2 | 9/2011 | Michelson |
| 8,025,697 B2 | 9/2011 | Abdelgany |
| 8,034,109 B2 | 10/2011 | Zwirkoski |
| 8,038,718 B2 | 10/2011 | Palm et al. |
| 8,043,376 B2 | 10/2011 | Falahee |
| 8,043,381 B2 | 10/2011 | Hestad et al. |
| 8,070,754 B2 | 12/2011 | Fabian et al. |
| 8,133,173 B2 | 3/2012 | Miles et al. |
| 8,133,232 B2 | 3/2012 | Levy et al. |
| 8,137,404 B2 | 3/2012 | Lopez et al. |
| 8,163,026 B2 | 4/2012 | Gray |
| 8,182,423 B2 | 5/2012 | Miles et al. |
| 8,187,334 B2 | 5/2012 | Curran et al. |
| 8,192,356 B2 | 6/2012 | Miles et al. |
| 8,206,423 B2 | 6/2012 | Siegal |
| 8,236,058 B2 | 8/2012 | Fabian et al. |
| 8,241,358 B2 | 8/2012 | Butler et al. |
| 8,246,622 B2 | 8/2012 | Siegal et al. |
| 8,246,686 B1 | 8/2012 | Curran et al. |
| 8,251,997 B2 | 8/2012 | Michelson |
| 8,267,939 B2 | 9/2012 | Cipoletti et al. |
| 8,303,458 B2 | 11/2012 | Fukano et al. |
| 8,317,798 B2 | 11/2012 | Lim et al. |
| 8,323,344 B2 | 12/2012 | Galley et al. |
| 8,328,852 B2 | 12/2012 | Zehavi et al. |
| 8,343,046 B2 | 1/2013 | Miles et al. |
| 8,343,224 B2 | 1/2013 | Lynn et al. |
| 8,361,148 B2 | 1/2013 | Malberg et al. |
| 8,361,156 B2 | 1/2013 | Curran et al. |
| 8,377,137 B2 | 2/2013 | Sournac et al. |
| 8,388,527 B2 | 3/2013 | Miles et al. |
| 8,409,291 B2 | 4/2013 | Blackwell et al. |
| 8,425,612 B2 | 4/2013 | Perez-Cruet et al. |
| 8,486,148 B2 | 7/2013 | Butler et al. |
| 8,486,149 B2 | 7/2013 | Saidha et al. |
| 8,506,630 B2 | 8/2013 | Wardlaw |
| 8,506,635 B2 | 8/2013 | Palmatier et al. |
| 8,506,636 B2 | 8/2013 | Dye |
| 8,523,944 B2 | 9/2013 | Jimenez et al. |
| 8,535,380 B2 | 9/2013 | Greenhalgh et al. |
| 8,551,173 B2 | 10/2013 | Lechmann et al. |
| 8,574,301 B2 | 11/2013 | Curran et al. |
| 8,579,909 B2 | 11/2013 | Burkus et al. |
| 8,579,977 B2 | 11/2013 | Fabian |
| 8,591,589 B2 | 11/2013 | Mccombe et al. |
| 8,608,804 B2 | 12/2013 | Curran et al. |
| 2001/0016741 A1 | 8/2001 | Burkus et al. |
| 2001/0039949 A1 | 11/2001 | Loubser |
| 2001/0056280 A1 | 12/2001 | Underwood et al. |
| 2002/0007129 A1 | 1/2002 | Marino |
| 2002/0010392 A1 | 1/2002 | Desai |
| 2002/0019637 A1 | 2/2002 | Frey et al. |
| 2002/0058950 A1 | 5/2002 | Winterbottom et al. |
| 2002/0068936 A1 | 6/2002 | Burkus et al. |
| 2002/0072686 A1 | 6/2002 | Hoey et al. |
| 2002/0077632 A1 | 6/2002 | Tsou |
| 2002/0116008 A1 | 8/2002 | Lin et al. |
| 2002/0123744 A1 | 9/2002 | Reynard |
| 2002/0123780 A1 | 9/2002 | Grill et al. |
| 2002/0161415 A1 | 10/2002 | Cohen et al. |
| 2002/0165550 A1 | 11/2002 | Frey et al. |
| 2002/0193843 A1 | 12/2002 | Hill et al. |
| 2003/0004574 A1 | 1/2003 | Ferree |
| 2003/0023306 A1 | 1/2003 | Liu et al. |
| 2003/0028249 A1 | 2/2003 | Baccelli et al. |
| 2003/0032966 A1 | 2/2003 | Foley et al. |
| 2003/0070682 A1 | 4/2003 | Wilson et al. |
| 2003/0083688 A1 | 5/2003 | Simonson |
| 2003/0100950 A1 | 5/2003 | Moret |
| 2003/0105503 A1 | 6/2003 | Marino |
| 2003/0105528 A1 | 6/2003 | Shimp et al. |
| 2003/0109928 A1 | 6/2003 | Pasquet et al. |
| 2003/0139648 A1 | 7/2003 | Foley et al. |
| 2003/0139812 A1 | 7/2003 | Garcia et al. |
| 2003/0139813 A1 | 7/2003 | Messerli |
| 2003/0149341 A1 | 8/2003 | Clifton |
| 2003/0149438 A1 | 8/2003 | Nichols et al. |
| 2003/0176924 A1 | 9/2003 | Burdett |
| 2003/0225405 A1 | 12/2003 | Weiner |
| 2003/0236544 A1 | 12/2003 | Lunsford et al. |
| 2004/0010318 A1 | 1/2004 | Ferree |
| 2004/0024408 A1 | 2/2004 | Burkus et al. |
| 2004/0133280 A1 | 7/2004 | Trieu |
| 2004/0153155 A1 | 8/2004 | Chung et al. |
| 2004/0176775 A1 | 9/2004 | Burkus et al. |
| 2004/0199084 A1 | 10/2004 | Kelleher et al. |
| 2004/0199251 A1 | 10/2004 | McCombe et al. |
| 2004/0210315 A1 | 10/2004 | Li et al. |
| 2004/0225228 A1 | 11/2004 | Ferree |
| 2004/0249459 A1 | 12/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0059971 A1 | 3/2005 | Michelson |
| 2005/0075578 A1 | 4/2005 | Gharib et al. |

(56) References Cited

U.S. PATENT DOCUMENTS

| | | |
|---|---|---|
| 2005/0080320 A1 | 4/2005 | Lee et al. |
| 2005/0149035 A1 | 7/2005 | Pimenta et al. |
| 2005/0177235 A1* | 8/2005 | Baynham et al. ......... 623/17.11 |
| 2005/0182454 A1 | 8/2005 | Gharib et al. |
| 2005/0187625 A1 | 8/2005 | Wolek et al. |
| 2005/0192575 A1 | 9/2005 | Pacheco |
| 2005/0197702 A1 | 9/2005 | Coppes et al. |
| 2005/0203538 A1 | 9/2005 | Lo et al. |
| 2005/0256576 A1* | 11/2005 | Moskowitz et al. ....... 623/17.12 |
| 2005/0261769 A1* | 11/2005 | Moskowitz et al. ....... 623/17.11 |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0074488 A1 | 4/2006 | Abdou |
| 2006/0106462 A1 | 5/2006 | Tsou |
| 2006/0129244 A1 | 6/2006 | Ensign |
| 2006/0142858 A1 | 6/2006 | Colleran et al. |
| 2006/0142864 A1 | 6/2006 | Cauthen |
| 2006/0178746 A1* | 8/2006 | Bartish et al. .............. 623/17.13 |
| 2006/0195191 A1 | 8/2006 | Sweeney, II et al. |
| 2006/0224078 A1 | 10/2006 | Hoey et al. |
| 2006/0235423 A1 | 10/2006 | Cantu |
| 2006/0253202 A1 | 11/2006 | Lipov |
| 2006/0265077 A1 | 11/2006 | Zwirkoski |
| 2007/0016097 A1 | 1/2007 | Farquhar et al. |
| 2007/0067034 A1 | 3/2007 | Chirico et al. |
| 2007/0093906 A1 | 4/2007 | Hudgins et al. |
| 2007/0118222 A1 | 5/2007 | Lang |
| 2007/0162135 A1 | 7/2007 | Segal et al. |
| 2007/0168043 A1 | 7/2007 | Ferree |
| 2007/0179612 A1 | 8/2007 | Johnson et al. |
| 2007/0191945 A1 | 8/2007 | Yu et al. |
| 2007/0198062 A1 | 8/2007 | Miles et al. |
| 2007/0219634 A1 | 9/2007 | Greenhalgh et al. |
| 2007/0233272 A1 | 10/2007 | Boyce et al. |
| 2007/0260314 A1 | 11/2007 | Biyani |
| 2007/0260318 A1 | 11/2007 | Lawson |
| 2007/0276499 A1 | 11/2007 | Paul et al. |
| 2007/0288007 A1 | 12/2007 | Burkus et al. |
| 2007/0293782 A1 | 12/2007 | Marino |
| 2008/0015701 A1 | 1/2008 | Garcia et al. |
| 2008/0039942 A1 | 2/2008 | Bergeron |
| 2008/0058606 A1 | 3/2008 | Miles et al. |
| 2008/0058838 A1 | 3/2008 | Steinberg |
| 2008/0064976 A1 | 3/2008 | Kelleher et al. |
| 2008/0064977 A1 | 3/2008 | Kelleher et al. |
| 2008/0065144 A1 | 3/2008 | Marino et al. |
| 2008/0065178 A1 | 3/2008 | Kelleher et al. |
| 2008/0065219 A1 | 3/2008 | Dye |
| 2008/0071191 A1 | 3/2008 | Kelleher et al. |
| 2008/0097164 A1 | 4/2008 | Miles et al. |
| 2008/0103597 A1 | 5/2008 | Lechmann et al. |
| 2008/0114367 A1 | 5/2008 | Meyer |
| 2008/0119853 A1 | 5/2008 | Felt et al. |
| 2008/0119937 A1 | 5/2008 | McCombe et al. |
| 2008/0133015 A1 | 6/2008 | Lechmann et al. |
| 2008/0195210 A1 | 8/2008 | Milijasevic et al. |
| 2008/0208345 A1 | 8/2008 | Hurlbert et al. |
| 2008/0249628 A1 | 10/2008 | Altarac et al. |
| 2008/0281346 A1* | 11/2008 | Greenhalgh et al. ........... 606/191 |
| 2008/0300465 A1 | 12/2008 | Feigenwinter et al. |
| 2008/0312743 A1 | 12/2008 | Vila et al. |
| 2009/0030423 A1 | 1/2009 | Puno |
| 2009/0048676 A1* | 2/2009 | Fabian, Jr. ................. 623/17.16 |
| 2009/0062422 A1 | 3/2009 | Nakamura et al. |
| 2009/0076607 A1 | 3/2009 | Aalsma et al. |
| 2009/0082872 A1 | 3/2009 | Beger |
| 2009/0093882 A1 | 4/2009 | Oh et al. |
| 2009/0099569 A1 | 4/2009 | Beger |
| 2009/0124860 A1 | 5/2009 | Miles et al. |
| 2009/0138050 A1 | 5/2009 | Ferree |
| 2009/0143859 A1 | 6/2009 | McClellan, III et al. |
| 2009/0143860 A1 | 6/2009 | Burd et al. |
| 2009/0157186 A1 | 6/2009 | Magerl |
| 2009/0192403 A1 | 7/2009 | Gharib et al. |
| 2009/0204016 A1 | 8/2009 | Gharib et al. |
| 2009/0210063 A1 | 8/2009 | Barrett |
| 2009/0222099 A1 | 9/2009 | Liu et al. |
| 2009/0234454 A1 | 9/2009 | Siegal |
| 2009/0248092 A1 | 10/2009 | Bellas et al. |
| 2009/0265008 A1* | 10/2009 | Thibodeau ................. 623/17.16 |
| 2009/0326543 A1 | 12/2009 | Fabian, Jr. |
| 2010/0016973 A1 | 1/2010 | DeVilliers et al. |
| 2010/0023128 A1 | 1/2010 | Malberg |
| 2010/0069783 A1 | 3/2010 | Miles et al. |
| 2010/0106250 A1 | 4/2010 | Abdou |
| 2010/0114107 A1 | 5/2010 | Trieu |
| 2010/0130827 A1 | 5/2010 | Pimenta et al. |
| 2010/0152603 A1 | 6/2010 | Miles et al. |
| 2010/0160738 A1 | 6/2010 | Miles et al. |
| 2010/0168858 A1 | 7/2010 | Hardenbrook et al. |
| 2010/0174146 A1 | 7/2010 | Miles |
| 2010/0174148 A1 | 7/2010 | Miles et al. |
| 2010/0198263 A1 | 8/2010 | Siegal et al. |
| 2010/0256764 A1 | 10/2010 | Tsuang et al. |
| 2010/0256766 A1 | 10/2010 | Hibri et al. |
| 2010/0286779 A1* | 11/2010 | Thibodeau ................. 623/17.11 |
| 2010/0286787 A1 | 11/2010 | Villiers et al. |
| 2010/0292799 A1 | 11/2010 | Hansell et al. |
| 2010/0292801 A1 | 11/2010 | Hansell et al. |
| 2011/0009970 A1 | 1/2011 | Puno |
| 2011/0015742 A1 | 1/2011 | Hong |
| 2011/0035011 A1 | 2/2011 | Cain |
| 2011/0046740 A1 | 2/2011 | Chen et al. |
| 2011/0066192 A1 | 3/2011 | Frasier et al. |
| 2011/0112642 A1 | 5/2011 | Tohmeh |
| 2011/0125270 A1 | 5/2011 | Paul et al. |
| 2011/0196496 A1 | 8/2011 | McCombe et al. |
| 2011/0276141 A1 | 11/2011 | Caratsch |
| 2011/0313530 A1 | 12/2011 | Gharib et al. |
| 2011/0319997 A1 | 12/2011 | Glerum et al. |
| 2011/0320000 A1 | 12/2011 | O'Neil et al. |
| 2012/0004732 A1 | 1/2012 | Goel et al. |
| 2012/0071977 A1 | 3/2012 | Oglaza et al. |
| 2012/0078374 A1 | 3/2012 | Villiers et al. |
| 2012/0083887 A1 | 4/2012 | Purcell et al. |
| 2012/0083889 A1 | 4/2012 | Purcell et al. |
| 2012/0089228 A1* | 4/2012 | Poulos ....................... 623/17.16 |
| 2012/0089231 A1 | 4/2012 | Prestigiacomo |
| 2012/0123546 A1 | 5/2012 | Medina |
| 2012/0158141 A1 | 6/2012 | Johnson et al. |
| 2012/0179261 A1 | 7/2012 | Soo |
| 2012/0209386 A1 | 8/2012 | Triplett et al. |
| 2012/0209388 A1 | 8/2012 | Curran et al. |
| 2012/0215316 A1 | 8/2012 | Mohr et al. |
| 2012/0215317 A1 | 8/2012 | Curran et al. |
| 2012/0238822 A1 | 9/2012 | Miles |
| 2012/0238893 A1 | 9/2012 | Farquhar et al. |
| 2012/0271422 A1 | 10/2012 | Miller et al. |
| 2012/0277875 A1 | 11/2012 | Arnin |
| 2012/0290094 A1 | 11/2012 | Lim et al. |
| 2012/0296433 A1 | 11/2012 | Farin |
| 2012/0310048 A1 | 12/2012 | Siegal et al. |
| 2012/0310350 A1* | 12/2012 | Farris et al. ................. 623/17.16 |
| 2012/0310352 A1* | 12/2012 | DiMauro et al. ........... 623/17.16 |
| 2013/0006363 A1 | 1/2013 | Ullrich et al. |
| 2013/0023997 A1 | 1/2013 | Razian et al. |
| 2013/0035762 A1 | 2/2013 | Siegal et al. |
| 2013/0041471 A1 | 2/2013 | Siegal et al. |
| 2013/0110239 A1 | 5/2013 | Siegal et al. |
| 2013/0138214 A1 | 5/2013 | Greenhalgh et al. |
| 2013/0138216 A1 | 5/2013 | Curran et al. |
| 2013/0144387 A1 | 6/2013 | Walker et al. |
| 2013/0144390 A1 | 6/2013 | Curran et al. |
| 2013/0173004 A1 | 7/2013 | Greenhalgh et al. |
| 2013/0197648 A1 | 8/2013 | Boehm et al. |
| 2013/0245771 A1 | 9/2013 | Michelson |

FOREIGN PATENT DOCUMENTS

| | | |
|---|---|---|
| DE | 299 08 259 | 7/1999 |
| DE | 19710392 C1 | 7/1999 |
| DE | 100 48 790 | 4/2002 |
| EP | 0 334 116 | 9/1989 |

(56) References Cited

FOREIGN PATENT DOCUMENTS

| | | |
|---|---|---|
| EP | 369603 | 5/1990 |
| EP | 517030 | 5/1992 |
| EP | 0515912 A2 | 12/1992 |
| EP | 0 567 424 | 10/1993 |
| EP | 667127 | 8/1995 |
| EP | 706876 | 4/1996 |
| EP | 716840 | 6/1996 |
| EP | 737448 | 10/1996 |
| EP | 796593 | 9/1997 |
| EP | 880938 | 2/1998 |
| EP | 809974 | 4/1998 |
| EP | 809975 | 4/1998 |
| EP | 811356 | 4/1998 |
| EP | 0 972 538 | 1/2000 |
| EP | 1 002 500 | 5/2000 |
| EP | 1043002 A2 | 10/2000 |
| EP | 1813228 A2 | 8/2007 |
| EP | 1941847 A1 | 7/2008 |
| EP | 1980222 A1 | 10/2008 |
| EP | 2446860 A1 | 5/2012 |
| EP | 2526882 A1 | 11/2012 |
| FR | 2 795 624 | 1/2001 |
| FR | 2900814 A1 | 11/2007 |
| FR | 2913331 A1 | 9/2008 |
| FR | 2951370 A1 | 4/2011 |
| JP | 793186 | 5/1990 |
| JP | 10-14928 | 3/1996 |
| JP | 2006223667 A | 8/2006 |
| JP | 2010158345 A1 | 7/2010 |
| KR | 3019990007098 | 11/1999 |
| KR | 20020042627 A | 6/2002 |
| WO | 90/00037 | 1/1990 |
| WO | 91/06261 | 5/1991 |
| WO | 92/14423 | 9/1992 |
| WO | 93/01771 | 2/1993 |
| WO | 94/04100 | 3/1994 |
| WO | 94/10928 | 5/1994 |
| WO | 94/28824 | 12/1994 |
| WO | 95/01810 | 1/1995 |
| WO | 95/08306 | 3/1995 |
| WO | WO-9525485 A1 | 9/1995 |
| WO | 96/08205 | 3/1996 |
| WO | 96/17564 | 3/1996 |
| WO | 96/41582 | 12/1996 |
| WO | 97/00702 | 1/1997 |
| WO | 97/20513 | 6/1997 |
| WO | 97/33525 | 9/1997 |
| WO | 97/37620 | 10/1997 |
| WO | 98/09586 | 3/1998 |
| WO | 98/14142 | 4/1998 |
| WO | 98/17208 | 4/1998 |
| WO | 98/23324 | 6/1998 |
| WO | 98/25539 | 6/1998 |
| WO | 99/08627 | 2/1999 |
| WO | WO-9905994 A1 | 2/1999 |
| WO | 99/38461 | 8/1999 |
| WO | 99/52446 | 10/1999 |
| WO | 00/27291 | 5/2000 |
| WO | 00/38574 | 7/2000 |
| WO | 00/44288 | 8/2000 |
| WO | 00/45712 | 8/2000 |
| WO | 00/45713 | 8/2000 |
| WO | 00/66217 | 11/2000 |
| WO | 00/67645 | 11/2000 |
| WO | WO-0103616 A1 | 1/2001 |
| WO | 01/08563 | 2/2001 |
| WO | 01/37728 | 5/2001 |
| WO | 01/41681 | 6/2001 |
| WO | 01/49333 | 7/2001 |
| WO | 01/60263 | 8/2001 |
| WO | WO-0178798 A1 | 10/2001 |
| WO | WO-0182844 A2 | 11/2001 |
| WO | 02/054960 | 7/2002 |
| WO | 02/058780 | 8/2002 |
| WO | 02/071953 | 9/2002 |
| WO | 02/087678 | 11/2002 |
| WO | 03/005887 | 1/2003 |
| WO | WO-03020169 A2 | 3/2003 |
| WO | 03/026482 | 4/2003 |
| WO | WO-03026538 A1 | 4/2003 |
| WO | 03/037170 | 5/2003 |
| WO | 2005/013805 | 2/2005 |
| WO | 2005/030318 | 4/2005 |
| WO | WO-2005051246 A2 | 6/2005 |
| WO | WO-2005089679 A1 | 9/2005 |
| WO | 2006/042241 | 4/2006 |
| WO | 2006/066217 | 6/2006 |
| WO | WO-2006113586 A2 | 10/2006 |
| WO | WO-2007050640 A2 | 5/2007 |
| WO | WO-2007089858 A2 | 8/2007 |
| WO | WO-2007121320 A2 | 10/2007 |
| WO | WO-2008088139 A1 | 7/2008 |
| WO | WO-2008132322 A2 | 11/2008 |
| WO | WO-2009123649 A1 | 10/2009 |
| WO | WO-2010008353 A1 | 1/2010 |
| WO | WO-2010092613 A1 | 8/2010 |
| WO | WO-2012065753 A1 | 5/2012 |
| WO | WO-2012137031 A1 | 10/2012 |

OTHER PUBLICATIONS

Dirksmeier et al., "Microendoscopic and Open Laminotomy and Discectomy in Lumbar Disc Disease" *Seminars in Spine Surgery*, 1999, 11(2): 138-146.
METRx Delivered Order Form, 1999, 13 pages.
Medtronic Sofamor Danek "METRx™ MicroDiscectomy System," *Medtronic Sofamor Danek USA*, 2000, 21 pgs.
Medtronic Sofamor Danek "METRx System Surgical Technique," 2004, 22 pages.
"MetRx System MicroEndoscopic Discectomy: An Evolution in Minimally Invasive Spine Surgery," *Sofamor Danek*, 1999, 6 pages.
Smith and Foley "MetRx System MicroEndoscopic Discectomy: Surgical Technique" *Medtronic Sofamor Danek*, 2000, 24 pages.
"Sofamor Danek MED Microendoscopic Discectomy System Brochure" including Rapp "New endoscopic lumbar technique improves access preserves tissue" Reprinted with permission from: *Orthopedics Today*, 1998, 18(1): 2 pages.
Japanese Patent Office JP Patent Application No. 2006-528306 Office Action with English Translation, Jun. 10, 2009, 4 pages.
Plaintiffs' Preliminary Invalidity Contentions re U.S. Pat. Nos. 7,207,949; 7,470,236 and 7,582,058, Sep. 18, 2009, 19 pages.
Plaintiffs' Preliminary Invalidity Contentions-Appendices, Sep. 18, 2009, 191 pages.
Plaintiffs' Supplemental Preliminary Invalidity Contentions re U.S. Pat. Nos. 7,207,949, 7,470,236, and 7,582,058, Sep. 29, 2009, 21 pages.
Plaintiffs' Supplemental Preliminary Invalidity Contentions-Appendices, Sep. 29, 2009, 294 pages.
Axon 501(k) Notification: Epoch 2000 Neurological Workstation, Dec. 3, 1997, 464 pages.
Foley and Smith, "Microendoscopic Discectomy," *Techniques in Neurosurgery*, 1997, 3(4):301-307.
Medtronic Sofamor Danek "UNION™ / UNION-L™ Anterior & Lateral Impacted Fusion Devices: Clear choice of stabilization," *Medtronic Sofamor Danek*, 2000, 4 pages.
NuVasive Vector™ Cannulae, 2000, 1 page.
NuVasive Triad™ Tri-Columnar Spinal EndoArthrodesis™ via Minimally Invasive Guidance, 2000, 1 page (prior to Sep. 25, 2003).
NuVasive Triad™ Cortical Bone Allograft, 2000, 1 page (prior to Sep. 25, 2003).
NuVasive Vertebral Body Access System, 2000, 1 page.
Marina, "New Technology for Guided Navigation with Real Time Nerve Surveillance for Minimally Invasive Spine Discectomy & Arthrodesis," *Spineline*, 2000, p. 39.
NuVasive "INS-1 Screw Test," 2001, 10 pages.
NuVasive letter re 510k Neuro Vision JJB System, Oct. 16, 2001, 5 pages.
NuVasive letter re 510k Guided Arthroscopy System, Oct. 5, 1999, 6 pages.

(56) References Cited

OTHER PUBLICATIONS

NuVasive letter re 510k INS-1 Intraoperative Nerve Surveillance System, Nov. 13, 2000, 7 pages.
"NuVasiveTM Receives Clearance to Market Two Key Elem Minimally Invasive Spine Surgery System," Nov. 27, 2001, 20 pages.
Schick et al., "Microendoscopic lumbar discectomy versus open surgery: an intraoperative EMG study," *Eur Spine J*, 2002, 11: 20-26.
NuVasive letter re: 510(k) for Neurovision JJB System (Summary), Sep. 25, 2001, 28 pages.
NuVasive letter re: Special 510(k) Premarket Notification: Neurovision JJB System (Device Description), Jul. 3, 2003, 18 pages.
NuVasive letter re: Special 510(k) Premarket Notification: Neurovision JJB System (Device Description), Mar. 1, 2004, 16 pages.
NuVasive letter re: Special 510(k) Premarket Notification: Neurovision JJB System (Device Description), May 26, 2005, 17 pages.
NuVasive letter re: 510(k) Premarket Notification: Neurovision JJB System (Device Description), Jun. 24, 2005, 16 pages.
NuVasive letter re: Special 510(k) Premarket Notification: Neurovision JJB System (Device Description), Sep. 14, 2006, 17 pages.
NuVasive 510(k) Premarket Notification: Neurovision JJB System (Device Description), Aug. 20, 2007, 8 pages.
NuVasive letter re: 510(k) Premarket Notification: Guided Spinal Arthroscopy System (Device Description), Feb. 1, 1999, 40 pages.
NuVasive 510(k) Premarket Notification: Spinal System (Summary), Apr. 12, 2004, 10 pages.
NuVasive 510(k) Summary NIM Monitor, Sep. 4, 1998, 4 pages.
NuVasive correspondence re 510(k) Premarket Notification INS-1 Intraoperative Nerve Surveillance System: Section IV Device Description, pp. 12-51 (prior to Sep. 25, 2003).
Isley et al., "Recent Advances in Intraoperative Neuromonitoring of Spinal Cord Function: Pedicle Screw Stimulation Techniques," *American Journal of Electroneurodiagnostic Technology*, Jun. 1997, 37(2): 93-126.
Mathews et al., "Laparoscopic Discectomy with Anterior Lumbar Interbody Fusion," *SPINE*, 1995, 20(16): 1797-1802.
Rose et al., "Persistently Electrified Pedicle Stimulation Instruments in Spinal Instrumentation: Techniques and Protocol Development," *SPINE*, 1997, 22(3): 334-343.
"Electromyography System," International Search report from International Application No. PCT/US00/32329, Apr. 27, 2001, 9 pages.
"Nerve Proximity and Status Detection System and Method," International Search Report from International Application No. PCT/US01/18606, Oct. 18, 2001, 6 pages.
"Relative Nerve Movement and Status Detection System and Method," International Search Report from International Application No. PCT/US01/18579, Jan. 15, 2002, 6 pages.
"System and Method for Determining Nerve Proximity Direction and Pathology During Surgery," International Search Report from International Application No. PCT/US02/22247, Mar. 27, 2003, 4 pages.
"System and Methods for Determining Nerve Direction to a Surgical Instrument," International Search Report from International Application No. PCT/US03/02056, Aug. 12, 2003, 5 pages.
"Systems and Methods for Performing Percutaneous Pedicle Integrity Assessments," International Search Report from International Application No. PCT/US02/35047, Aug. 11, 2003, 5 pages.
"Systems and Methods for Performing Surgery Procedures and Assessments," International Search Report from International Application No. PCT/US02/30617, Jun. 5, 2003, 4 pages.
Lenke et al., "Triggered Electromyographic Threshold for Accuracy of Pedicle Screw Placement," *Spine*, 1995, 20(4): 1585-1591.
"Brackmann II EMG System," *Medical Electronics*, 1999, 4 pages.
"Neurovision SE Nerve Locator/Monitor", RLN Systems Inc. Operators Manual, 1999, 22 pages.
"The Brackmann II EMG Monitoring System," Medical Electronics Co. Operator's Manual Version 1.1, 1995, 50 pages.
"The Nicolet Viking IV," Nicolet Biomedical Products, 1999, 6 pages.

Anderson et al., "Pedicle screws with high electrical resistance: a potential source of error with stimulus-evoked EMG," *Spine*, Department of Orthopaedic Surgery University of Virginia, Jul. 15, 2002, 27(14): 1577-1581.
Bose et al., "Neurophysiologic Monitoring of Spinal Nerve Root Function During Instrumented Posterior Lumber Spine Surgery," *Spine*, 2002, 27(13):1444-1450.
Calancie et al., "Stimulus-Evoked EMG Monitoring During Transpedicular Lumbosacral Spine Instrumentation" *Spine*, 1994, 19(24): 2780-2786.
Clements et al., "Evoked and Spontaneous Electromyography to Evaluate Lumbosacral Pedicle Screw Placement," *Spine*, 1996, 21(5): 600-604.
Danesh-Clough et al. ,"The Use of Evoked EMG in Detecting Misplaced Thoracolumbar Pedicle Screws," *Spine*, Orthopaedic Department Dunedin Hospital, Jun. 15, 2001, 26(12): 1313-1316.
Darden et al., "A Comparison of Impedance and Electromyogram Measurements in Detecting the Presence of Pedicle Wall Breakthrough," *Spine*, Charlotte Spine Center, North Carolina, Jan. 15, 1998, 23(2): 256-262.
Ebraheim et al., "Anatomic Relations Between the Lumbar Pedicle and the Adjacent Neural Structures," *Spine*, Department of Orthopaedic Surgery Medical College of Ohio, Oct. 15, 1997, 22(20): 2338-2341.
Ford et al. "Electrical Characteristics of Peripheral Nerve Stimulators Implications for Nerve Localization," *Regional Anesthesia*, 1984, 9: 73-77.
Glassman et al., "A Prospective Analysis of Intraoperative Electromyographic Monitoring of Pedicle Screw Placement With Computed Tomographic Scan Confirmation," *Spine*, 1995, 20(12): 1375-1379.
Greenblatt et al., "Needle Nerve Stimulator-Locator: Nerve Blocks with a New Instrument for Locating Nerves," *Anesthesia & Analgesia*, 1962, 41(5): 599-602.
Haig, "Point of view," *Spine*, 2002, 27(24): 2819.
Haig et al., "The Relation Among Spinal Geometry on MRI, Paraspinal Electromyographic Abnormalities, and Age in Persons Referred for Electrodiagnostic Testing of Low Back Symptoms," *Spine*, Department of Physical Medicine and Rehabilitation University of Michigan, Sep. 1, 2002, 27(17): 1918-1925.
Holland et al., "Higher Electrical Stimulus Intensities are Required to Activate Chronically Compressed Nerve Roots: Implications for Intraoperative Electromyographic Pedicle Screw Testing," *Spine*, Department of Neurology, Johns Hopkins University School of Medicine, Jan. 15, 1998, 23(2): 224-227.
Holland, "Intraoperative Electromyography During Thoracolumbar Spinal Surgery," *Spine*, 1998, 23(17): 1915-1922.
Journee et al., "System for Intra-Operative Monitoring of the Cortical Integrity of the Pedicle During Pedicle Screw Placement in Low-Back Surgery: Design and Clinical Results," *Sensory and Neuromuscular Diagnostic Instrumentation and Data Analysis I, 18th Annual International Conference on Engineering in Medicine and Biology Society*, Amsterdam, 1996, pp. 144-145.
Maguire et al., "Evaluation of Intrapedicular Screw Position Using Intraoperative Evoked Electromyography," *Spine*, 1995, 20(9): 1068-1074.
Martin et al. "Initiation of Erection and Semen Release by Rectal Probe Electrostimulation (RPE)," *The Journal of Urology*, The Williams & Wilkins Co., 1983, 129: 637-642.
Minahan et al., "The Effect of Neuromuscular Blockade on Pedicle Screw Stimulation Thresholds" *Spine*, Department of Neurology, Johns Hopkins University School of Medicine, Oct. 1, 2000, 25(19): 2526-2530.
Pither et al., "The Use of Peripheral Nerve Stimulators for Regional Anesthesia: Review of Experimental Characteristics Technique and Clinical Applications," *Regional Anesthesia*, 1985, 10:49-58.
Raj et al., "Infraclavicular Brachial Plexus Block—A New Approach" *Anesthesia and Analgesia*, 1973, (52)6: 897-904.
Raj et al., "The Use of Peripheral Nerve Stimulators for Regional Anesthesia," *Clinical Issues in Regional Anesthesia*, 1985, 1(4):1-6.
Raj et al., "Use of the Nerve Stimulator for Peripheral Blocks," *Regional Anesthesia*, Apr.-Jun. 1980, pp. 14-21.

(56) References Cited

OTHER PUBLICATIONS

Raymond et al., "The Nerve Seeker: A System for Automated Nerve Localization," *Regional Anesthesia*, 1992, 17(3): 151-162.

Shafik, "Cavernous Nerve Simulation through an Extrapelvic Subpubic Approach: Role in Penile Erection," *Eur. Urol*, 1994, 26: 98-102.

Toleikis et al., "The Usefulness of Electrical Stimulation for Assessing Pedicle Screw Replacements," *Journal of Spinal Disorder*, 2000, 13(4): 283-289.

Medtronic Sofamor Danek "UNION™ / UNION-L™ Anterior & Lateral Impacted Fusion Devices: Surgical Technique" *Medtronic Sofamor Danek*, 2001, 20 pages.

Defendant's Disclosure of Asserted Claims and Preliminary Infringement Contentions Regarding U.S. Pat. Nos. 7,207,949; 7,470,236 and 7,582,058, Aug. 31, 2009, 21 pages.

Bergey et al., "Endoscopic Lateral Transpsoas Approach to the Lumbar Spine," *Spine*, 2004, 29(15): 1681-1688.

Dezawa et al., "Retroperitoneal Laparoscopic Lateral Approach to the Lumbar Spine: A New Approach, Technique, and Clinical Trial," *Journal of Spinal Disorders*, 2000, 13(2): 138-143.

Gardocki, "Tubular diskectomy minimizes collateral damage: A logical progression moves spine surgery forward," *AAOS Now*, 2009, 5 pages.

Hovorka et al., "Five years' experience of retroperitoneal lumbar and thoracolumbar surgery," *Eur Spine J.*, 2000, 9(1): S30-S34.

Kossmann et al., "The use of a retractor system (SynFrame) for open, minimal invasive reconstruction of the anterior column of the thoracic and lumbar spine," *Eur Spine J.*, 2001, 10: 396-402.

Mayer, "A New Microsurgical Technique for Minimally Invasive Anterior Lumbar Interbody Fusion," *Spine*, 1997, 22(6): 691-699.

Mayer, "The ALIF Concept," *Eur Spine J.*, 2000, 9(1): S35-S43.

Mayer and Wiechert, "Microsurgical Anterior Approaches to the Lumbar Spine for Interbody Fusion and Total Disc Replacement," *Neurosurgery*, 2002, 51(2): 159-165.

McAfee et al., "Minimally Invasive Anterior Retroperitoneal Approach to the Lumbar Spine: Emphasis on the Lateral BAK," *Spine*, 1998, 23(13): 1476-1484.

Rao, et al. "Dynamic retraction of the psoas muscle to expose the lumbar spine using the retroperitoneal approach," *J. Neurosurg Spine*, 2006, 5: 468-470.

Wolfla et al., "Retroperitoneal lateral lumbar interbody fusion with titanium threaded fusion cages," *J. Neurosurg (Spine 1)*, 2002, 96: 50-55.

Larson and Maiman, "Surgery of the Lumbar Spine," Thieme Medical Publishers, Inc., 1999, pp. 305-319.

Medtronic XOMED Surgical Products, Inc., NIM-Response Nerve Integrity Monitor Intraoperative EMG Monitor User's Guide, Revision B, 2000, 47 pages.

"NuVasive's spine surgery system cleared in the US," Pharm & Medical Industry Week, Dec. 10, 2001, 1 page.

Pimenta, "Initial Clinical Results of Direct Lateral, Minimally Invasive Access to the Lumbar Spine for Disc Nucleus Replacement Using a Novel Neurophysiological Monitoring System." *The 9th IMAST*, May, 2002, 1 page.

Pimenta et al., "The Lateral Endoscopic Transpsoas Retroperitoneal Approach (Letra) for Implants in the Lumbar Spine," *World Spine II—Second Interdisciplinary Congress on Spine Care*, Aug. 2003, 2 pages.

Crock, H.V. MD., "Anterior Lumbar Interbody Fusion," Clinical Orthopaedics and Related Research, Number One Hundred Sixty Five, 1982, pp. 157-163, 13 pages.

Mayer and Brock, "Percutaneous endoscopic discectomy: surgical technique and preliminary results compared to microsurgical discectomy," *J. Neurosurg*, 1993, 78: 216-225.

Schaffer and Kambin, "Percutaneous Posterolateral Lumbar Discectomy and Decompression with a 6.9-Millimeter Cannula," *The Journal of Bone and Joint Surgery*, 1991, 73A(6): 822-831.

Friedman, "Percutaneous discectomy: An alternative to chemonucleolysis," *Neurosurgery*, 1983, 13(5): 542-547.

Request for Inter Partes Reexamination in re U.S. Pat. No. 7,905,840, dated Feb. 8, 2012, 204 pages.

Brau, "Chapter 22: Anterior Retroperitoneal Muscle-Sparing approach to L2-S1 of the Lumbar Spine," *Surgical Approaches to the Spine*. Robert G. Watkins, MD. (ed) 2003. pp. 165-181.

Kossmann et al., "Minimally Invasive Vertebral Replacement with Cages in Thoracic and Lumbar Spine," *European Journal of Trauma*, 2001, 27: 292-300.

Mayer H. M. (ed.) *Minimally Invasive Spine Surgery: A Surgical Manual*. 2000. 51 pages.

Pimenta et al., "Implante de protese de nucleo pulposo: analise inicial," *Journal Brasileiro de Neurocirurgia*, 2001, 12(2): 93-96.

Traynelis, "Spinal Arthroplasty," *Neurological Focus*, 2002, 13(2): 12 pages.

Zdeblick, Thomas A. (ed.). Anterior Approaches to the Spine. 1999. 43 pages.

Amended Complaint for *NuVasive, Inc.* v. *Globus Medical, Inc.*, Case No. 1:10-cv-0849 (D. Del., Oct. 5, 2010), 28 pages.

Request for Inter Partes Reexamination In re U.S. Pat. No. 7,819,801, dated Feb. 8, 2012, 89 pages.

Kossman et al., "The use of a retractor system (SynFrame) for open, minimal invasive reconstruction of the anterior column of the thoracic and lumbar spine," *Eur Spine J*, 2001, 10: 396-402.

de Peretti et al., "New possibilities in L2-L5 lumbar arthrodesis using a lateral retroperitoneal approach assisted by laparoscopy: preliminary results," *Eur Spine J*, 1996, 5: 210-216.

Litwin et al., "Hand-assisted laparoscopic surgery (HALS) with the handport system," *Annals of Surgery*, 2000, 231(5): 715-723.

Acland's Video Atlas of Human Anatomy, Section 3.1.7: Paravertebral Muscles. Available online: http://aclandanatomy.com/abstract/4010463. Accessed Jul. 11, 2012.

MedlinePlus, a Service of the U.S. National Library of Medicine and National Institutes of Health. Available online: http://www.nlm.nih.gov/medlineplus/. Accessed Jul. 11, 2012.

Baulot et al., Adjuvant Anterior Spinal Fusion Via Thoracoscopy, *Lyon Chirurgical*, 1994, 90(5): 347-351 including English Translation and Certificate of Translation.

Leu et al., "Percutaneous Fusion of the Lumbar Spine," *Spine*, 1992, 6(3): 593-604.

Rosenthal et al., "Removal of a Protruded Thoracic Disc Using Microsurgical Endoscopy," *Spine*, 1994, 19(9): 1087-1091.

Counterclaim Defendants' Corrected Amended Invalidity Contentions re U.S. Pat. Nos. 8,000,782; 8,005,535; 8,016,767; 8,192,356; 8,187,334; 8,361,156, D652,922; D666,294 re Case No. 3:12-cv-02738-CAB(MDD), dated Aug. 19, 2013, 30 pages.

Petition for Inter Partes Review IPR2014-00034, filed Oct. 8, 2013, 65 pages.

Petition for Inter Partes Review IPR2014-00035, filed Oct. 8, 2013, 65 pages.

Declaration of Lee Grant, from IPR2014-00034, Oct. 7, 2013, 36 pages.

Declaration of David Hacker from IPR2014-00034, Oct. 4, 2013, 64 pages.

NuVasive, Inc's Opening Claim Construction Brief Regarding U.S. Pat. Nos. 8,000,782; 8,005,535; 8,016,767; 8,192,356; 8,187,334; 8,361,156; D652,922; and 5,676,146 C2, filed Sep. 3, 2013, in *Warsaw Orthopedic, Inc.* v. *NuVasive, Inc.*, No. 3:12-cv-02738-CAB-MDD (S.D. Cal.)., 34 pages.

Petition for Inter Partes Review IPR2014-00073, filed Oct. 18, 2013, 65 pages.

Petition for Inter Partes Review IPR2014-00074, filed Oct. 18, 2013, 65 pages.

Petition for Inter Partes Review IPR2014-00075, filed Oct. 21, 2013, 66 pages.

Petition for Inter Partes Review IPR2014-00076, filed Oct. 21, 2013, 65 pages.

Petition for Inter Partes Review IPR2014-00081, filed Oct. 22, 2013, 64 pages.

Petition for Inter Partes Review IPR2014-00087, filed Oct. 22, 2013, 64 pages.

Declaration of Lee Grant, from IPR2014-00073, Oct. 9, 2013, 36 pages.

(56) References Cited

OTHER PUBLICATIONS

Declaration of David Hacker, from IPR2014-00073, Oct. 10, 2013, 64 pages.
U.S. Appl. No. 60/392,214, filed Jun. 26, 2002, 97 pages.
Amendment in reply to Feb. 15, 2012 Office Action in U.S. Appl. No. 12/635,418, dated Mar. 16, 2012, 24 pages.
Decision on Appeal in Inter Partes Reexamination Control U.S. Appl. No. 95/001,247, dated Mar. 18, 2013, 49 pages.
Declaration of Lee Grant, from IPR2014-00074, Oct. 9, 2013, 36 pages.
Declaration of David Hacker, from IPR2014-00074, Oct. 10, 2013, 64 pages.
Declaration of David Hacker, from IPR2014-00075, Oct. 10, 2013, 64 pages.
Amendment in reply to Action of Feb. 7, 2011 and Notice of May 12, 2011, in U.S. Appl. No. 11/789,284, dated May 17, 2011, 16 pages.
Notice of Allowance in U.S. Appl. No. 11/789,284, dated Jul. 18, 2011, 8 pages.
Office action from U.S. Appl. No. 11/789,284, dated Feb. 7, 2011, 10 pages.
Merriam-Webster's Collegiate Dictionary, p. 65 (10th ed. 1998).
Declaration of Lee Grant, from IPR2014-00076, Oct. 9, 2013, 36 pages.
Moed et al., "Evaluation of Intraoperative Nerve-Monitoring During Insertion of an Iliosacral Implant in an Animal Model, *Journal of Bone and Joint Surgery*," 1999, 81-A(11): 9.
Declaration of Lee Grant, from IPR2014-0081, Oct. 9, 2013, 36 pages.
Declaration of David Hacker from IPR2014-00081, Oct. 10, 2013, 64 pages.
U.S. Appl. No. 60/325,424, filed Sep. 25, 2001, 346 pages.
Declaration of Lee Grant, from IPR2014-0087, Oct. 9, 2013, 36 pages.
Declaration of David Hacker from IPR2014-00087, Oct. 10, 2013, 64 pages.
Request for Inter Partes Reexamination in re: U.S. Pat. No. 7,691,057, dated Feb. 8, 2012, 50 pages.
Declaration of Daniel Schwartz, Ph.D. from IPR2014-00034, Oct. 7, 2013, 1056 pages.
Declaration of Daniel Schwartz, Ph.D. from IPR2014-00035, Oct. 7, 2013, 661 pages.
510(K) No. K002677, approved by the FDA on Nov. 13, 2000, 634 pages.
510(K) No. K013215, approved by the FDA on Oct. 16, 2001, 376 pages.
Declaration of Robert G. Watkins, from IPR2014-00073, Oct. 18, 2013, 1101 pages.
Declaration of Daniel Schwartz, from IPR2014-00073, Oct. 12, 2013, 1226 pages.
Declaration of Robert G. Watkins, from IPR2014-00074, Oct. 18, 2013, 548 pages.
Declaration of Daniel Schwartz, from IPR2014-00074, Oct. 12, 2013, 565 pages.
Declaration of Robert G. Watkins, from IPR2014-00075, Oct. 18, 2013, 674 pages.
Declaration of Daniel Schwartz, from IPR2014-00075, Oct. 12, 2013, 1107 pages.
Declaration of Robert G. Watkins, from IPR2014-00076, Oct. 18, 2013, 543 pages.
Declaration of Daniel Schwartz, from IPR2014-00076, Oct. 12, 2013, 1247 pages.
Declaration of David Hacker, from IPR2014-00076, Oct. 10, 2013, 64 pages.
Declaration of Daniel Schwartz, from IPR2014-0081, Oct. 21, 2013, 585 pages.
Declaration of Daniel Schwartz from IPR2014-0087, Oct. 21, 2013, 585 pages.
Patent Owner NuVasive Inc's Preliminary Response from IPR2014-00034, dated Jan. 15, 2014, 66 pages.
Patent Trial and Appeal Board Decision from IPR 2014-00034, dated Apr. 8, 2014, 35 pages.
Patent Owner NuVasive Inc's Preliminary Response from IPR2014-00035, dated Jan. 15, 2014, 42 pages.
Patent Trial and Appeal Board Decision from IPR 2014-00035, dated Apr. 8, 2014, 12 pages.
Patent Owner NuVasive Inc's Preliminary Response from IPR2014-00073, dated Jan. 31, 2014, 64 pages.
Patent Trial and Appeal Board Decision from IPR 2014-00073, dated Apr. 8, 2014, 34 pages.
Patent Owner NuVasive Inc's Preliminary Response from IPR2014-00074, dated Jan. 31, 2014, 68 pages.
Patent Trial and Appeal Board Decision from IPR 2014-00074, dated Apr. 8, 2014, 28 pages.
Patent Owner NuVasive Inc's Preliminary Response from IPR2014-00075, dated Jan. 31, 2014, 54 pages.
Patent Trial and Appeal Board Decision from IPR 2014-00075, dated Apr. 8, 2014, 23 pages.
Patent Owner NuVasive Inc's Preliminary Response from IPR2014-00076, dated Jan. 31, 2014, 58 pages.
Patent Trial and Appeal Board Decision from IPR 2014-00076, dated Apr. 8, 2014, 11 pages.
Patent Owner NuVasive Inc's Preliminary Response from IPR2014-00081, dated Jan. 31, 2014, 47 pages.
Patent Trial and Appeal Board Decision from IPR 2014-00081, dated Apr. 8, 2014, 31 pages.
Patent Owner NuVasive Inc's Preliminary Response from IPR2014-00087, dated Jan. 31, 2014, 51 pages.
Patent Trial and Appeal Board Decision from IPR 2014-00087, dated Apr. 8, 2014, 31 pages.
Final Written Decision from IPR 2014-00034, dated Apr. 3, 2015, 48 pages.
Final Written Decision from IPR 2014-00073, dated Apr. 3, 2015, 36 pages.
Final Written Decision from IPR 2014-00074, dated Apr. 3, 2015, 31 pages.
Final Written Decision from IPR 2014-00075, dated Apr. 3, 2015, 39 pages.
Final Written Decision from IPR 2014-00081, dated Apr. 3, 2015, 44 pages.
Final Written Decision from IPR 2014-00087, dated Apr. 3, 2015, 36 pages.
Alleyne, Cargill, H., et al., "Current and future approaches to lumbar disc surgery: A literature review", *Medscape Orthopedics & Sports Medicine*, 1, [www.medscape.com/Medscape/OrthoSportsMed/1997/v01.n11/.../mos3057], (1997).
Benini, et al., "Undercutting decompression and posterior fusion with translaminar facet screw fixation in degenerative lumbar spinal stenosis: Technique and results", *Neuro-Orthopedics*, 17/18, 159-172 (1995).
Berry, et al., "A morphometric study of human lumbar and selected thoracic vertebrae, study of selected vertebrae" *Spine* 12(4):362-367 (1996).
CoRoent® XL & XLR Marketing Brochure (9004225 B.0), *NuVasive, Inc.*, 2006, 2 pages.
CoRoent® XL & XLR Marketing Brochure (9004225 C.0), *NuVasive, Inc.*, 2007, 2 pages.
CoRoent® XL Marketing Brochure (9500039 A.0), *NuVasive, Inc.*, 2006, 8 pages.
CoRoent™ Marketing Brochure (9004001 A.0), *NuVasive, Inc.*, 2004, 2 pages.
CoRoent™ Marketing Brochure (9004001 C.0), *NuVasive, Inc.*, 2005, 2 pages.
CoRoent™ XL & XLR Marketing Brochure (9004225 A.0), *NuVasive, Inc.*, 2005, 2 pages.
Crock, H. V., "A Short Practice of Spinal Surgery", Second, revised edition, published by Springer-Verlag/Wein, New York (1993).
Declaration of Mary Phelps Regarding Telamon Verte-Stack PEEK Vertebral Body Spacer, dated Aug. 13, 2013, 9 pages.
Declaration of Richard A. Hynes, M.D. Regarding U.S. Pat. No. 8,187,334, dated Aug. 14, 2013, 74 pages.
Declaration of Richard A. Hynes, M.D. Regarding U.S. Pat. No. 8,361,156, dated Aug. 14, 2013, 74 pages.

(56) References Cited

OTHER PUBLICATIONS

Declaration of Steven D. DeRidder regarding U.S. Patent Application Publication No. 2002/0165550, Jul. 30, 2013, 5 pages.
Edeland, H.G., "Some additional suggestions for an intervertebral disc prosthesis", *Journal of Biomedical Engineering*, 7:57-62 (1985).
Kambin, et al., "History and current status of percutaneous arthroscopic disc surgery", *Spine*, 21(24S):57S-61S (1996).
Kemp, H. B. S., "Anterior fusion of the spine for infective lesions in adults", *Journal of Bone & Joint Surgery*, 55B(4):715-734 (1973).
Medtronic Sofamor Danek USA, Inc. "Boomerang I Verte-Stack PEEK Vertebral Body Brochure," 2003, 6 pages.
Medtronic Sofamor Danek USA, Inc. "Boomerang I Verte-Stack PEEK Vertebral Body Spacer Implant," Apr. 26, 2001, 8 pages.
Medtronic Sofamor Danek USA, Inc. "Boomerang II Verte-Stack PEEK Vertebral Body Spacer Brochure," 2004, 4 pages.
Medtronic Sofamor Danek USA, Inc. "Boomerang II Verte-Stack PEEK Vertebral Body Spacer Implant," Dec. 17, 2003, 9 pages.
Medtronic Sofamor Danek USA, Inc. "Boomerang Prototype Verte-Stack PEEK Vertebral Body Spacer Implant," May 7, 2000, 8 pages.
Medtronic Sofamor Danek USA, Inc. "PCR PEEK Cement Restrictor Brochure," 2001, 2 pages.
Medtronic Sofamor Danek USA, Inc. "PCR PEEK Cement Restrictor Implant," Oct. 2, 2001, 17 pages.
Medtronic Sofamor Danek USA, Inc. "Telamon Verte-Stack PEEK Vertebral Body Spacer Brochure I," 2003, 2 pages.
Medtronic Sofamor Danek USA, Inc. "Telamon Verte-Stack PEEK Vertebral Body Spacer Brochure II," 2003, 10 pages.
Medtronic Sofamor Danek USA, Inc. "Telamon Verte-Stack PEEK Vertebral Body Spacer Implant," Oct. 2, 2001, 6 pages.
Nuvasive, Inc., Corrected Final Invalidity Contentions Regarding U.S. Pat. No. 5,860,973, U.S. Pat. No. 6,592,586 and U.S. Pat. No. 6,945,933 filed in the United States District Court, Southern District of California on Jun. 14, 2010 (and 23 appendices).
Petition for Inter Partes Review of U.S. Pat. No. 8,187,334 Pursuant to 35 U.S.C. 311-319, 37 C.F.R. 42, dated Aug. 14, 2013, 64 pages.
Petition for Inter Partes Review of U.S. Pat. No. 8,361,156 Pursuant to 35 U.S.C. 311-319, 37 C.F.R. 42, dated Aug. 14, 2013, 64 pages.
Second Petition for Inter Partes Review of U.S. Pat. No. 8,187,334 Pursuant to 35 U.S.C. 311-319, 37 C.F.R. 42, dated Aug. 14, 2013, 64 pages.
Second Petition for Inter Partes Review of U.S. Pat. No. 8,361,156 Pursuant to 35 U.S.C. 311-319, 37 C.F.R. 42, dated Aug. 14, 2013, 64 pages.
Stein, et al., "Percutaneous facet joint fusion: Preliminary experience", *Journal of Vascular and Interventional Radiology*, 4:69-74 (1993).
Synthes Vertebral Spacer-PR Brochure, *Synthes Spine*, 2002, 2 pages.
Synthesis Spine Vertebral Spacer-PR Implant, Jun. 2002, 2 pages.
Synthesis Spine Vertebral Spacer-TR Implant, Aug. 2002, 2 pages.
Telamon Implantation Guide, *Medtronic Sofamor Danek*, 2003, 10 pages.
Telamon Verte-Stack PEEK Vertebral Body Spacer Brochure, *Medtronic Sofamor Danek*, 2003, 2 pages.
Vamvanij, et al., "Surgical treatment of internal disc disruption: An outcome study of four fusion techniques", *Journal of Spinal Disorders*, 11(5):375-382 (1998).
Zhou et al., Geometrical dimensions of the lower lumbar vertebrae-analysis of data from digitised CT images, *Eur Spine J*, 2000, 9: 242-248.
Patent Owner NuVasive Inc.'s Preliminary Response in IPR2013-00504, dated Nov. 25, 2013, 40 pages.
Decision denying Institution of Inter Partes review in IPR2013-00504, dated Feb. 13, 2014, 9 pages.
Patent Owner NuVasive Inc.'s Preliminary Response in IPR2013-00506, dated Nov. 25, 2013, 38 pages.
Decision denying Institution of Inter Partes review in IPR2013-00506, dated Feb. 13, 2014, 21 pages.
NuVasive Inc's Patent Owner Response in IPR2013-00506, dated May 21, 2014, 66 pages.
Declaration of Dr. Hansen A. Yuan from IPR2013-00506, dated May 21, 2014, 63 pages.
Synthes SVS-PR Guide, *Synthes Spine*, 2002, 8 pages.
Synthes Vertebral Spacer—AR brochure, *Synthesis Spine*, 2006, 4 pages.
Saber Surgical Technique/Product Catalogue, *DePuy Spine*, 2004, 12 pages.
Petition for Inter Partes Review of U.S. Pat. No. 8,361,156 Pursuant to 35 U.S.C. 311-319, 37 C.F.R. 42, dated Mar. 5, 2014, 64 pages.
Patent Owner NuVasive Inc.'s Preliminary Response in IPR2013-00507, dated Nov. 25, 2013, 29 pages.
Decision denying Institution of Inter Partes review in IPR2013-00507, dated Feb. 13, 2014, 15 pages.
NuVasive Inc's Patent Owner Response in IPR2013-00507, dated May 21, 2014, 50 pages.
Declaration of Dr. Hansen A. Yuan from IPR2013-00507, dated May 21, 2014, 85 pages.
Patent Owner NuVasive Inc.'s Preliminary Response in IPR2013-00508, dated Nov. 25, 2013, 38 pages.
Decision denying Institution of Inter Partes review in IPR2013-00508, dated Feb. 13, 2014, 14 pages.
NuVasive Inc's Patent Owner Response in IPR2013-00508, dated May 21, 2014, 66 pages.
Declaration of Dr. Hansen A. Yuan from IPR2013-00508, dated May 21, 2014, 85 pages.
Final Written Decision in *Medtronic, Inc. v. NuVasive, Inc.*, Case IPR2013-00507, dated Feb. 11, 2015, 14 pages.
Final Written Decision in *Medtronic, Inc. v. NuVasive, Inc.*, Case IPR2013-00508, dated Feb. 11, 2015, 19 pages.

* cited by examiner

EXPANDABLE SPINAL FUSION IMPLANTS AND RELATED METHODS

CROSS REFERENCE TO RELATED APPLICATIONS

This application claims the benefit of the filing date of U.S. Provisional Application No. 61/553,895, which was filed on Oct. 31, 2011. The contents of U.S. Application No. 61/553,895 are incorporated by reference in their entirety as a part of this application.

BACKGROUND

The present application relates to spinal fusion surgery, and more particularly, to a system for promoting fusion across an intervertebral disc space.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The expandable system of spinal fusion implants disclosed herein boasts a variety of inventive features and components that warrant patent protection, both individually and in combination.

Figure 1:
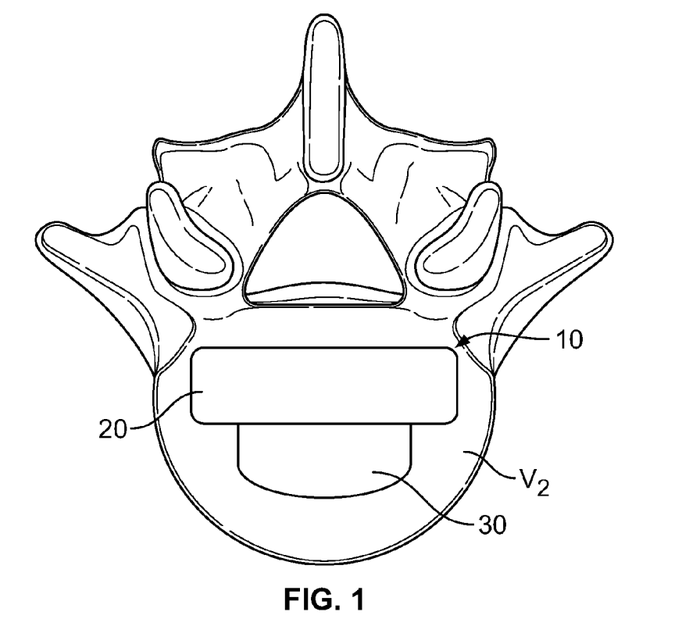
FIG. 1 is a top view of the expandable system of spinal fusion implants in its insertion state resting on the superior endplate of a vertebral body.
Figure 2:
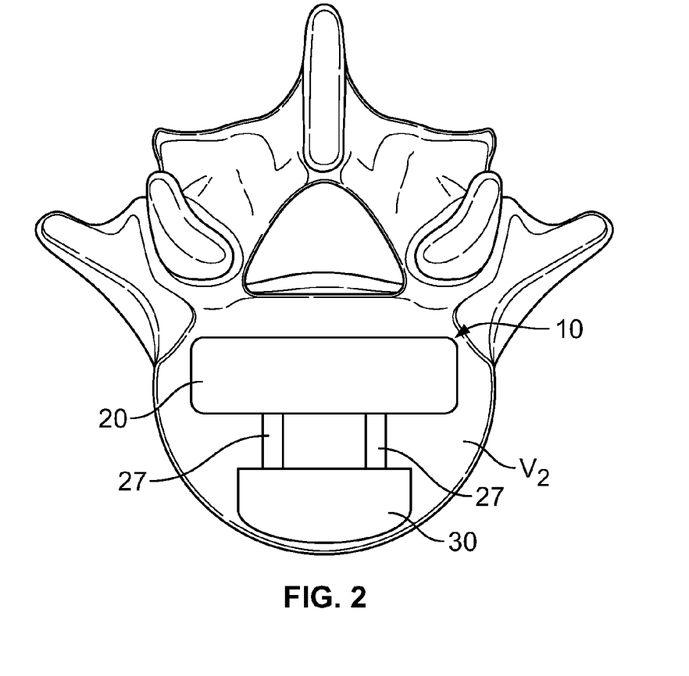
FIG. 2 is a top view of the expandable system of spinal fusion implants in its expanded state resting on the superior endplate of a vertebral body.
Figure 3:
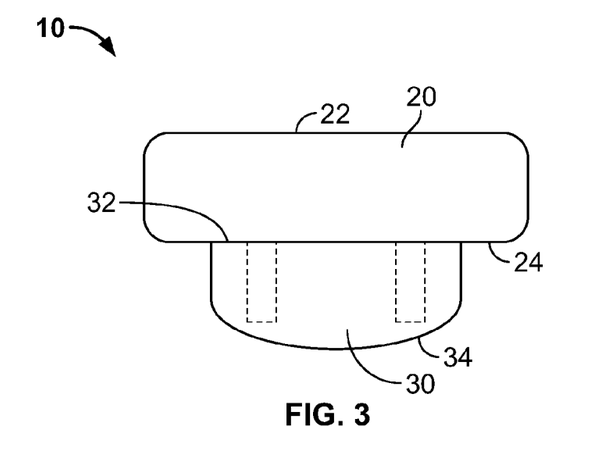
FIG. 3 is a top view of the expandable system of spinal fusion implants in its insertion state, prior to insertion into an intervertebral disc space.
Figure 4A:
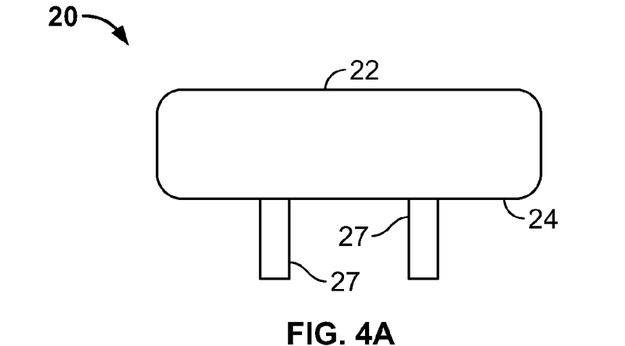
FIG. 4a is a top view of the first implant of the expandable system of spinal fusion implants.
Figure 4B:
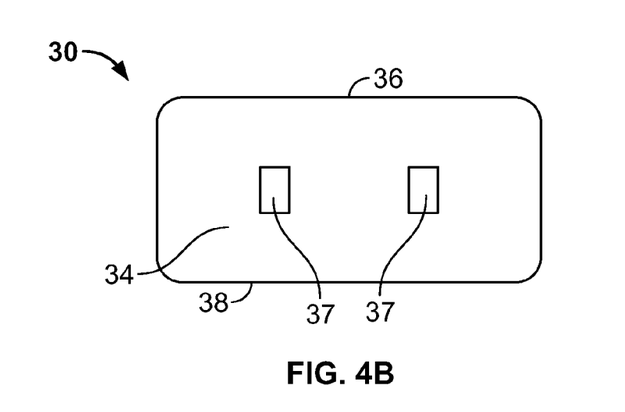
FIG. 4b is a posterior view of the second implant of the expandable system of spinal fusion implants.

FIGS. 1-9 illustrate an expandable system of spinal fusion implants for promoting fusion across an intervertebral disc space according to an exemplary embodiment. The system 10 includes a first intervertebral implant 20 and a second intervertebral implant 30, dimensioned for insertion into an intervertebral disc space via a lateral approach. The expandable system of implants 10 is configured to be inserted into the intervertebral disc space in a smaller profile collapsed state (as shown in FIGS. 1 and 3) and manipulated into an expanded state (as shown in FIG. 2) within the intervertebral disc space. The first implant 20 and second implant 30 are constructed of any suitable biocompatible material. According to an exemplary embodiment, the system of implants 10 is constructed primarily of radiolucent material and comprises radiopaque markers to aid in the positioning of the implant during surgery or visualization of the implants in postoperative imaging.

The first implant 20 of the expandable system 10 has a posterior wall 22, an anterior wall 24, a leading end lateral wall 23, a trailing end lateral wall 25, a first bone contacting (top) surface 26 and a second bone contacting (bottom) surface 28. The second implant 30 of the expandable system 10 has a posterior wall 32, an anterior wall 34, a leading end lateral wall 33, a trailing end lateral wall 35, a first bone contacting (top) surface 36 and a second bone contacting (bottom) surface 38. The leading end walls 23, 33 and the trailing end walls 25, 35 may also be referred to as the distal end 23, 33 and proximal end 25, 35, respectively. The expandable system 10 is configured such that in the smaller profile insertion state, the anterior wall 24 of the first implant 20 is in close proximity with the posterior wall 32 of the second implant 30. Upon complete insertion into the intervertebral disc space in the insertion state, the second implant 30 is moved anteriorly; away from the first implant 20 such that the distance between the anterior wall 24 of the first implant 20 and the posterior wall 32 of the second implant 30 increases. Preferably, the anterior wall 34 of the second implant 30 rests on the hard cortical bone anterior rim of the inferior vertebral body $V_2$ of the disc space when the system of implants 10 is in its fully expanded state.

According to one embodiment, the first implant 20 and second implant 30 each have a length extending between the respective proximal end 25, 35 and distal end 23, 33. It is contemplated that the length of each of the first implant 20 and second implant 30 may vary according to the needs of the user. For example, the length of the first implant may be dimensioned to span the width of the intervertebral disc space, such that the distal end 23 of the implant rests on the hard cortical bone rim on the distal lateral aspect of the inferior vertebral body $V_2$ of the intervertebral disc space, and the proximal end 25 of the first implant 20 rests on the hard cortical bone of the proximal lateral aspect of the inferior vertebral body $V_2$ of the intervertebral disc space. According to another exemplary embodiment, the length of the first implant 20 is not greater that the greatest depth dimension of the intervertebral disc space, as measured from the anterior most aspect of the inferior vertebral body $V_2$ to the posterior aspect of the inferior vertebral body $V_2$. The length of the second implant 30 may be equal to or less than the length of the first implant 20.

Similarly, the first implant 20 and second implant 30 each have a height extending between the top surface 26, 36 and the bottom surface 28, 38. The height of the first 20 and second implants 30 is dimensioned to restore the height of the intervertebral disc space to a healthy height. The height of the first implant 20 may be equal to, greater than or less than the height of the second implant 30, depending on the desired degree of kyphosis or lordosis at the treated intervertebral level. Further, the first implant 20 and second implant 30 each have a width extending from the anterior surface 24, 34 to the posterior surface 22, 32. The width of the first implant 20 may be equal to, greater than or less than the width of the second implant 30.

According to an exemplary embodiment, the first implant further includes one or more first mating elements 27 for coupling the first implant 20 to the second implant 30 during insertion into the intervertebral disc space. In the exemplary embodiment shown in FIGS. 1-9, the first mating element 27 are male mating elements projecting from the anterior surface 24 of the first implant 20. According to this embodiment, the second implant 30 further includes one or more second mating elements 37 that complement the first mating element(s) 27 of the first implant 27. As shown in FIGS. 1-9, the second mating element 37 is a female mating element, dimensioned to receive therein the first mating element 27 of the first implant 20. However, it will be appreciated that the male mating element may instead extend from the second implant 30 and the complementary female mating element formed on the first implant 20. According to the exemplary embodiment, the first mating elements 27 of the first implant 20 are slidably received within the second mating elements 37 of the second implant 30, such that the alignment of the second implant 30 with respect to the first implant 20 is maintained during insertion of the system of implants 10 and while the second implant 20 is displaced anteriorly upon complete insertion of the system 10 into the intervertebral disc space.

Figure 5:
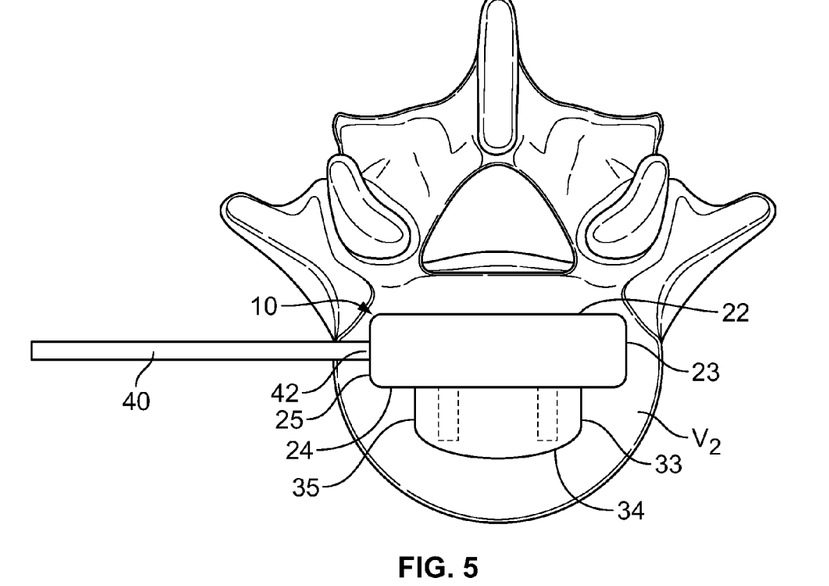
FIG. 5 illustrates the expandable system of implants in its insertion state while attached to an inserter.
Figure 6:
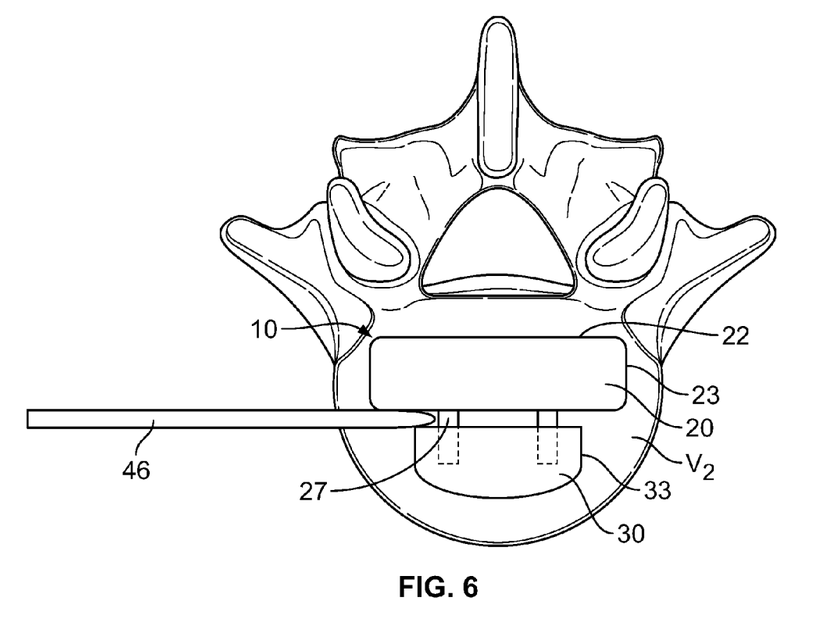
FIGS. 6-7 illustrate the method of expanding the system of implants once the system is inserted into the intervertebral disc space.
Figure 7:
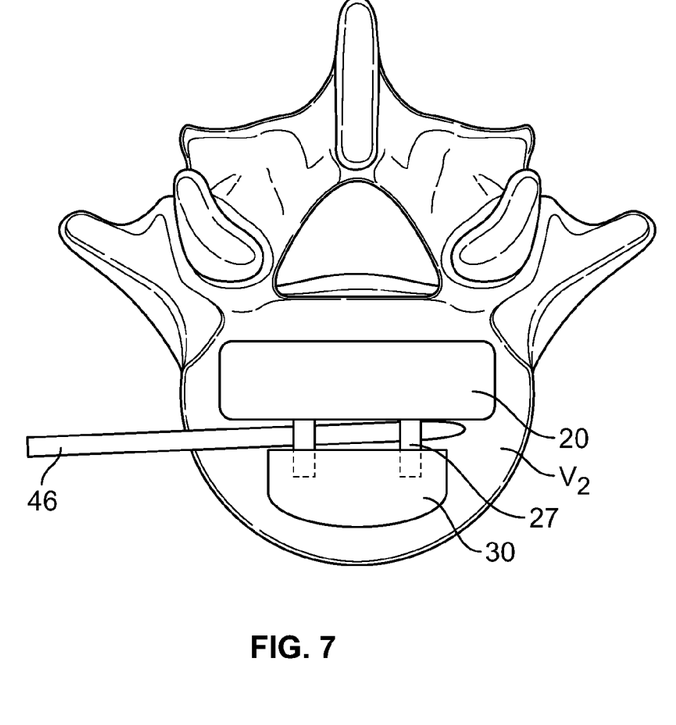
Figure 8:
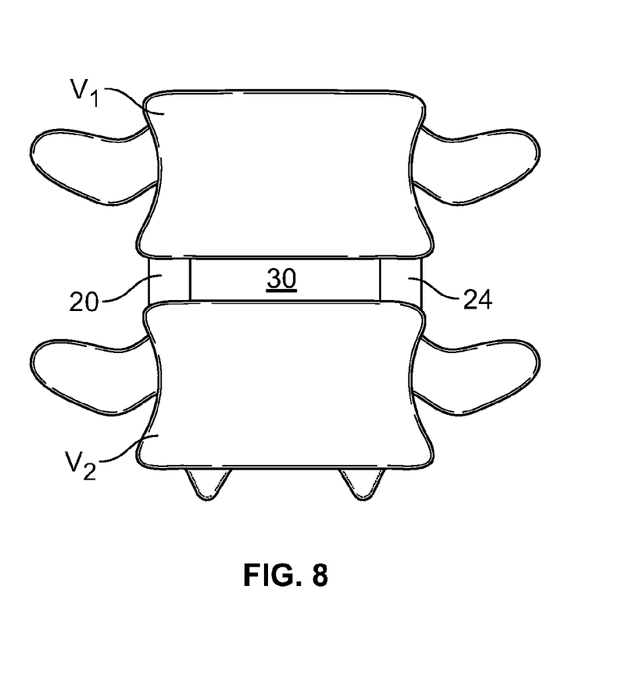
FIG. 8 is an anterior view of the expandable system of implants post-insertion and expansion within the intervertebral disc space.
Figure 9:
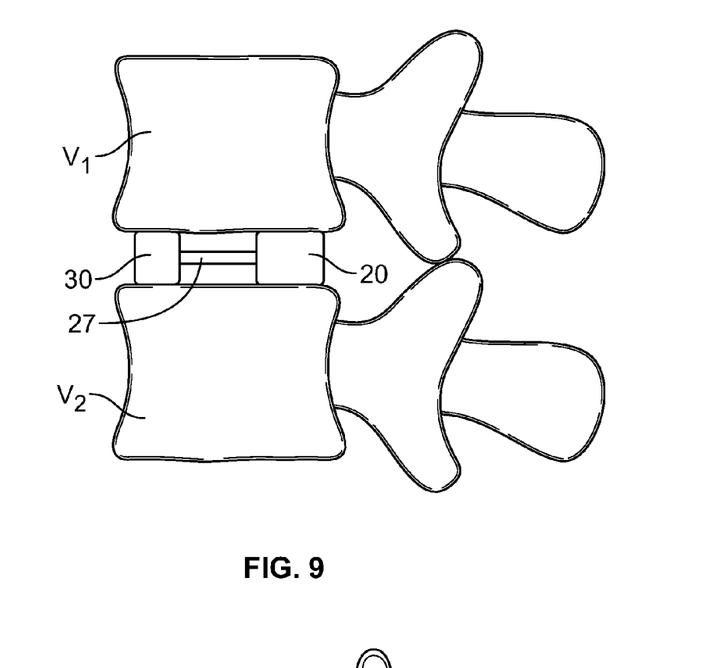
FIG. 9 is a lateral view of the expandable system of implants post-insertion and expansion within the intervertebral disc space.

FIGS. 5-7 illustrate the steps of a method of inserting the expandable system of spinal fusion implants 10 into an intervertebral disc space. According to the exemplary embodiment shown in FIGS. 5-7, the first implant 20 and second implant 30 are coupled via the first mating element 27 and the second mating element 37. The system of implants 10 is coupled to an insertion tool 40 on the distal end 25 of the first implant 20. The system of implants 20 is inserted into the intervertebral disc space in a smaller profile, collapsed state, as best shown in FIG. 5. Upon complete insertion into the disc space, a positioning tool 46 is used to displace the second implant 30 anteriorly within the disc space, away from the first implant 20. Displacement of the second implant 30 relative to the substantially stationary first implant 20 creates a greater distance between the anterior surface 24 of the first implant 20 and the posterior surface 32 of the second implant. The second implant 30 is displaced anteriorly until the anterior wall 34 of the second implant is resting on the cortical anterior rim of the inferior vertebral body $V_2$, as best illustrated by FIGS. 2 and 9. According to an exemplary embodiment, the first implant 20 is positioned within the intervertebral disc space such that at least a portion of the posterior wall 22 of the first implant 20 is resting on the cortical posterior aspect of the inferior vertebral body $V_2$. According to one exemplary embodiment, the space created between the first implant 20 and the second implant 30 after the anterior displacement of the second implant 30 is packed with bone growth promoting material. By way of example only, the bone growth enhancing material is autograft bone, allograft bone, bone graft substitute, a combination thereof, or any other suitable fusion enhancing scaffold.

While FIGS. 5-7 show the system of implants 10 coupled to a single inserter, an alternative embodiment is also contemplated wherein the system of implants 10 is coupled to two separate inserters, a first inserter coupled to the distal end of the first implant 20 and the second inserter coupled to the distal end 35 of the second implant 30. According to this alternative embodiment, the first 20 and second implants 30 may or may not be coupled via mating elements 27, 37.

Figure 10:
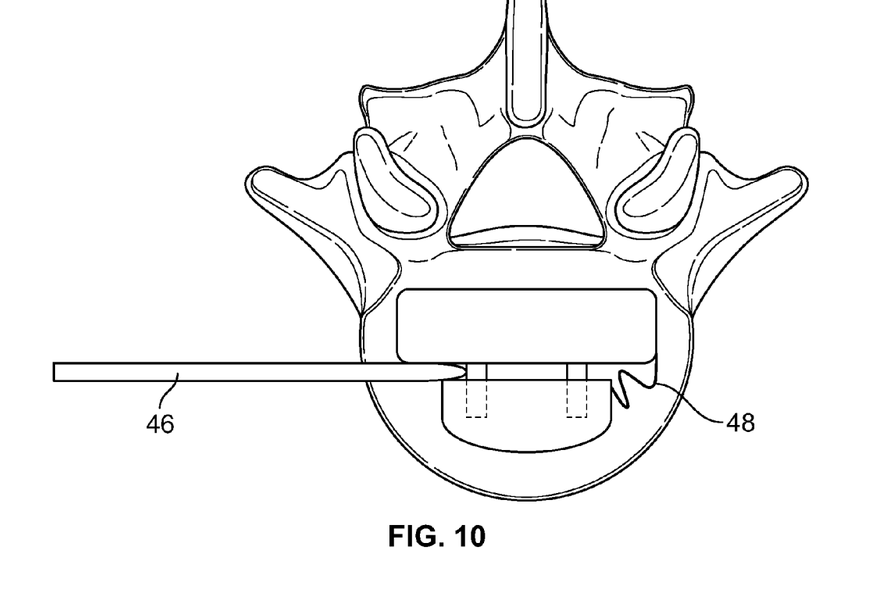
FIGS. 10-12 illustrate a method of expanding the system of implants according to an alternative embodiment.
Figure 11:
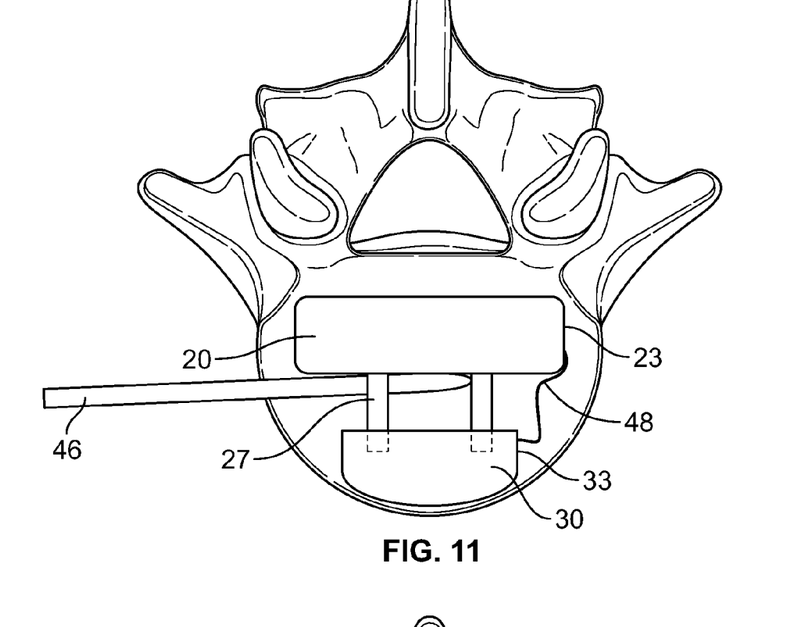
Figure 12:
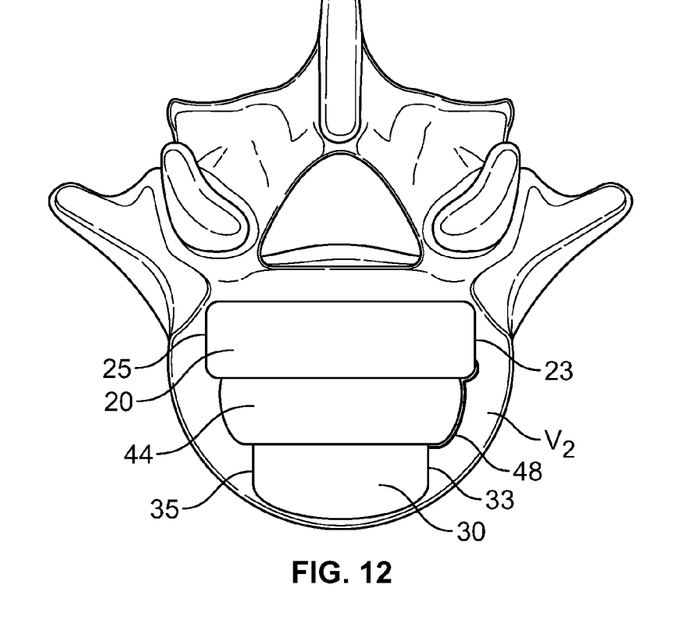

FIGS. 10-12 illustrate an alternative embodiment of the expandable system of spinal fusion implants. This alternative embodiment includes all of the features described above and is inserted according to the same method described above, but further includes a flexible tether 48 coupled to the distal ends 23, 33 of the first 20 and second 30 implants. When the system of implants 10 is in the collapsed insertion state, there is slack in the flexible tether 48, as shown in FIGS. 10 and 11. As the system of implants 10 is expanded to its fully expanded state, the flexible tether 48 becomes increasingly taut. When the system of implants 10 reaches its fully expanded state, the flexible tether 48 is taut and acts as a wall connecting the distal ends 23, 33 of the first 20 and second implant 30 and a barrier to maintain bone growth enhancing material within the gap between the first 20 and second implants 30 when the system of implants 10 is in its fully expanded state and filled with bone growth enhancing material 44, as best shown in FIG. 12.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method for promoting fusion across an intervertebral disc space, the method comprising the steps of:
   accessing an intervertebral disc space via a lateral approach;
   inserting an expandable system of spinal fusion implants in an insertion state into the intervertebral disc space, wherein said expandable system of spinal fusion implants comprises: a first implant having a length extending between a leading end and a trailing end, an anterior wall and a posterior wall, and a top surface and a bottom surface, wherein the length of the first implant spans the width of the interverterbral space from a first lateral aspect of a vertebral body adjacent the intervertebral space to a second lateral aspect of the vertebral body, a second implant having a leading end and a trailing end, an anterior wall and a posterior wall, and a top surface and a bottom surface; and a flexible element coupled to the leading end of the first implant and the leading end of the second implant;
   displacing said second implant anteriorly relative to first implant within the intervertebral disc space until the expandable system of spinal fusion implants achieves a fully expanded state, wherein the anterior wall of the second implant rests on an anterior cortical rim of an inferior vertebral body adjacent the intervertebral disc space, and wherein, in the fully expanded state, the posterior wall of the second implant is spaced apart anteriorly from the anterior wall of the first implant, thereby creating a gap extending from the anterior wall of the first implant to the posterior wall of the second implant.

2. The method of claim 1, further comprising the step of filling the gap between the first implant and the second implant with bone growth enhancing material.

3. The method of claim 1, wherein the second implant has a length extending between the leading end and the trailing end that is shorter than the length of the first implant.

4. The method of claim 1, wherein the first implant and the second implant are equal in height.

5. The method of claim 1, wherein the second implant has a maximum height that is greater than a maximum height of the first implant.

6. The method of claim 1, wherein the first implant is coupled to the second implant during insertion.

7. The method of claim 1, wherein the system of implants is inserted simultaneously using a single insertion tool.

8. The method of claim 1, wherein the first implant is inserted with a first insertion tool and the second implant is inserted with a second insertion tool.

\* \* \* \* \*